US006974639B2

(12) United States Patent
Tsuboyama et al.

(10) Patent No.: US 6,974,639 B2
(45) Date of Patent: Dec. 13, 2005

(54) METAL COORDINATION COMPOUND, LUMINESCENCE DEVICE AND DISPLAY APPARATUS

(75) Inventors: Akira Tsuboyama, Sagamihara (JP); Shinjiro Okada, Isehara (JP); Takao Takiguchi, Tokyo (JP); Seishi Miura, Sagamihara (JP); Takashi Moriyama, Kawasaki (JP); Jun Kamatani, Kawasaki (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/090,838

(22) Filed: Mar. 6, 2002

(65) Prior Publication Data

US 2003/0068536 A1 Apr. 10, 2003

(30) Foreign Application Priority Data

Mar. 8, 2001 (JP) .................................... 2001/064204
Feb. 20, 2002 (JP) .................................... 2002/042440

(51) Int. Cl.$^7$ .......................... H05B 33/14; C09K 11/06
(52) U.S. Cl. ...................... 428/690; 428/917; 313/504; 546/4; 544/225; 548/103; 257/88
(58) Field of Search ................................ 428/690, 917; 313/504, 506; 252/301.16; 257/40, 102, 103, 88; 546/4; 544/225; 548/103

(56) References Cited

U.S. PATENT DOCUMENTS

| | | | |
|---|---|---|---|
| 5,698,858 A | 12/1997 | Börner | 250/484.2 |
| 6,114,715 A | 9/2000 | Hamada | 257/72 |
| 2001/0019782 A1 * | 9/2001 | Igarashi et al. | 428/690 |
| 2001/0053462 A1 | 12/2001 | Mishima | 428/690 |
| 2002/0034656 A1 * | 3/2002 | Thompson et al. | 428/690 |

FOREIGN PATENT DOCUMENTS

| | | |
|---|---|---|
| EP | 1 138 746 A1 | 10/2001 |
| EP | 1 160 889 A2 | 12/2001 |
| EP | 1 175 128 A2 | 1/2002 |
| EP | 1 191 612 A2 | 3/2002 |
| EP | 1 919 613 A2 | 3/2002 |
| EP | 1 211 257 A2 | 6/2002 |
| JP | 8-319482 | 12/1996 |
| JP | 11-256148 | 9/1999 |
| JP | 11-329739 | 11/1999 |
| JP | 2001-257076 | 9/2001 |
| JP | 2001-313179 | 11/2001 |
| JP | 2001-357977 A | 12/2001 |
| WO | WO 00/70655 A1 | 11/2000 |
| WO | WO 01/08230 A1 | 2/2001 |
| WO | WO 01/41512 A1 | 6/2001 |
| WO | WO 01/72927 A1 | 10/2001 |
| WO | WO 01/91203 A2 | 11/2001 |
| WO | WO 02/02714 A2 | 1/2002 |
| WO | WO 02/15645 A1 | 2/2002 |
| WO | WO 02/45466 A1 | 6/2002 |
| WO | WO 02/066552 A1 * | 8/2002 |
| WO | WO 03/000661 A1 | 1/2003 |

OTHER PUBLICATIONS

Maestri et al., "Photochemistry and Luminescence of Cyclometallated Complexes", Advances in Photochemistry, vol. 17, 1992, pp. 1–68, no month.*
P.I. Djurovich et al., "Ir(III) Cyclometalated Complexes as Efficient Phosphorescent Emitters in Polymer Blend and Organic LEDs", Polymer Preprints, American Chemical Society, USA, vol. 41, No. 1, Mar. 2000, pp 770–771.
Dedeian, et al., "A New Synthetic Route to the Preparation of a Series of Strong Photoreducing Agents: *fac* Tris–Ortho–Metalated Complexes of Iridium(III) with Substituted 2–Phenylpyridines", Inorganic Chemistry, American Chemical Society, Easton, USA, vol. 30, No. 30, 1991, pp. 1685–1687.

(Continued)

*Primary Examiner*—Marie Yamnitzky
(74) *Attorney, Agent, or Firm*—Fitzpatrick, Cella, Harper & Scinto

(57) ABSTRACT

An electroluminescence device having a layer containing a specific metal coordination compound is provided. The metal coordination compound is represented by formula (1) below:

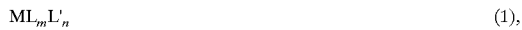

wherein M is a metal atom of Ir, Pt, Rh or Pd; L and L' are mutually different bidentate ligands; m is 1, 2 or 3 and n is 0, 1 or 2 with the proviso that m+n is 2 or 3; a partial structure $ML_m$ is represented by formula (2) shown below and a partial structure $ML'_n$ is represented by formula (3) or (4) shown below:

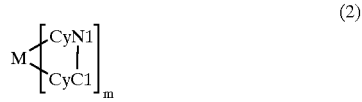

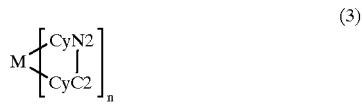

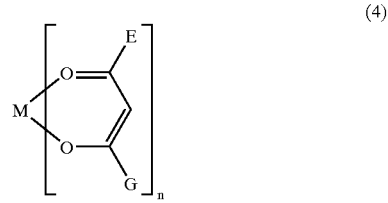

The metal coordination compound of the formula (1) is characterized by having at least one aromatic substituent for at least one of CyN1, CyN2, CyC1 and CyC2. The metal coordination compound having the aromatic substituent is effective in providing high-efficiency luminescence, long-term high luminance, and less deterioration by current passing.

10 Claims, 3 Drawing Sheets

OTHER PUBLICATIONS

C. Adachi, et al., "High–efficiency Organic Electrophosphorescent Devices with Tris(2–phenylpyridine) Iridium Doped into Electron–Transporting Materials", Applied Physics Letters, American Institute of Physics, New York, USA, vol. 77, No. 6, Aug. 2000, pp. 904–906.

M.J. Yang, et al., "Use of Poly(9–vinylcarbazole) as Host Material for Iridium Complexes in High–Efficiency Organic Light–Emitting Devices," Japanese Journal of Applied Physics, Publication Office Japanese Journal of Applied Physics, Tokyo, JP, vol. 39, No. 8A, Part 2, Aug. 1, 2000, pp. L828–L829.

R.C. Kwong, et al., "Organic Light–Emitting Devices Based on Phosphorescent Hosts and Dyes", Advanced Materials, VCH Verlagsgesellschaft, Weinheim, DE, vol. 12, No. 15, Aug. 2, 2000, pp. 1134–1138.

T. Tsutsui, et al., "High Quantum Efficiency in Organic Light–Emitting Devices with Iridium–Complex as a Triplet Emissive Center", Japanese Journal of Applied Physics, Publication Office Japanese Journal of Applied Physics, Tokyo, JP, vol. 38, No. 12B, Part 2, Dec. 15, 1999, pp. L1502–L1504.

S. Lamansky, et al., "Synthesis and Characterization of Phosphorescent Cyclometalated Iridium Complexes", Inorganic Chemistry, American Chemical Society, Easton, USA, vol. 40, No. 7, 2001, pp. 1704–1711, published on web Mar. 1, 2001.

Y. Wang, et al., "Highly Efficient Electroluminescent Materials Based on Fluorinated Organometallic Iridium Compounds", Applied Physics Letters, American Institute of Physics, New York, USA, vol. 79, No. 4, Jul. 23, 2001, pp. 449–451.

S. Lamansky, et al., "Molecularly Doped Polymer Light Emitting Diodes Utilizing Phosphorescent Pt(II) and Ir(III) Dopants", Organic Electronics, Elsevier, Amsterdam, NL, vol. 2, No. 1, Mar. 2001, pp. 53–62.

V.V. Grushin, et al., "New, Efficient Electroluminescent Materials Based on Organometallic Ir Complexes", Chemical Communications, Royal Society of Chemistry, GB, 2001, pp. 1494–1495.

M.G. Colombo, et al., "Facial Tris Cyclometalated $Rh^{3+}$ and $Ir^{3+}$ Complexes: Their Synthesis, Structure, and Optical Spectroscopic Properties", Inorg. Chem., 1994, vol. 33, pp. 545–550.

Z.X. Hong, et al., "Reduction of Self–Quenching Effect in Organic Electrophosphorescence Emitting Devices via the Use of Sterically Hindered Spacers in Phosphorescence Molecules", Advanced Materials, VCH Verlagsgesellschaft, Weinheim, DE, vol. 13, No. 16, Aug. 16, 2001, pp. 1245–1248.

C.H. Chen, "Recent Development in Molecular . . . Materials", Macromol. Symp. 125, (1997) pp. 1–48.

D.F. O'Brien et al., "Improved energy transfer . . . devices," Appl. Phys. Letters, vol. 74, No. 3, Jan. 18, 1999, pp. 442–444.

M.A. Baldo, "Very high–efficiency green organic . . . electrophosphorence", App. Phys. Letters, vol. 75, No. 1, Jul. 5, 1999, pp. 4–6.

* cited by examiner

METAL COORDINATION COMPOUND, LUMINESCENCE DEVICE AND DISPLAY APPARATUS

FIELD OF THE INVENTION AND RELATED ART

The present invention relates to a luminescence device, a display apparatus and a metal coordination compound therefor. More specifically, the present invention relates to a luminescence device employing an organic metal coordination compound having a formula (1) appearing hereinafter as a luminescence material so as to allow stable luminescence efficiency, a display apparatus including the luminescence device and the metal coordination compound adapted for use in the luminescence device.

An organic electroluminescence (EL) device has been extensively studied as a luminescence device with a high responsiveness and high efficiency.

The organic EL device generally has a sectional structure as shown in FIG. 1A or 1B (e.g., as described in "Macromol. Symp.", 125, pp. 1–48 (1997)).

Referring to the figures, the EL device generally has a structure including a transparent substrate 15, a transparent electrode 14 disposed on the transparent substrate 15, a metal electrode 11 disposed opposite to the transparent electrode 14, and a plurality of organic (compound) layers disposed between the transparent electrode 14 and the metal electrode 11.

Referring to FIG. 1, the EL device in this embodiment has two organic layers including a luminescence layer 12 and a hole transport layer 13.

The transparent electrode 14 may be formed of a film of ITO (indium tin oxide) having a larger work function to ensure a good hole injection performance into the hole transport layer. On the other hand, the metal electrode 11 may be formed of a layer of aluminum, magnesium, alloys thereof, etc., having a smaller work function to ensure a good electron injection performance into the organic layer(s).

These (transparent and metal) electrodes 14 and 11 may be formed in a thickness of 50–200 nm.

The luminescence layer 12 may be formed of, e.g., aluminum quinolinol complex (representative example thereof may include Alq3 described hereinafter) having an electron transporting characteristic and a luminescent characteristic. The hole transport layer 13 may be formed of, e.g., triphenyldiamine derivative (representative example thereof may include α-NPD described hereinafter) having an electron donating characteristic.

The above-described EL device exhibits a rectification characteristic, so that when an electric field is applied between the metal electrode 11 as a cathode and the transparent electrode 14 as an anode, electrons are injected from the metal electrode 11 into the luminescence layer 12 and holes are injected from the transparent electrodes 14.

The thus-injected holes and electrons are recombined within the luminescence layer 12 to produce excitons, thus causing luminescence. At that time, the hole transport layer 13 functions as an electron-blocking layer to increase a recombination efficiency at the boundary between the luminescence layer 12 and the hole transport layer 13, thus enhancing a luminescence efficiency.

Referring to FIG. 1B, in addition to the layers shown in FIG. 1A, an electron transport layer 16 is disposed between the metal electrode 11 and the luminescence layer 12, whereby an effective carrier blocking performance can be ensured by separating functions of luminescence, electron transport and hole transport, thus allowing effective luminescence.

The electron transport layer 16 may be formed of, e.g., oxadiazole derivatives.

In ordinary organic EL devices, fluorescence caused during a transition of luminescent center molecule from a singlet excited state to a ground state is used as luminescence.

On the other hand, not the above fluorescence (luminescence) via singlet exciton, phosphorescence (luminescence) via triplet exciton has been studied for use in organic EL device as described in, e.g., "Improved energy transfer in electrophosphorescent device" (D. F. O'Brien et al., Applied Physics Letters, Vol. 74, No. 3, pp. 442–444 (1999)) and "Very high-efficiency green organic light-emitting devices based on electrophosphorescence" (M. A. Baldo et al., Applied Physics Letters, Vol. 75, No. 1, pp. 4–6 (1999)).

The EL devices shown in these documents may generally have a sectional structure shown in FIG. 1C.

Referring to FIG. 1C, four organic layers including a hole transfer layer 13, a luminescence layer 12, an exciton diffusion-prevention layer 17, and an electron transport layer 16 are successively formed in this order on the transparent electrode (anode) 14.

In the above documents, higher efficiencies have been achieved by using four organic layers including a hole transport layer 13 of α-NPD (shown below), an electron transport layer 16 of Alq3 (shown below), an exciton diffusion-prevention layer 17 of BPC (shown below), and a luminescence layer 12 of a mixture of CBP (shown below) as a host material with Ir(ppy)₃ (shown below) or PtOEP (shown below) as a guest phosphorescence material doped into CBP at a concentration of ca. 6 wt. %.

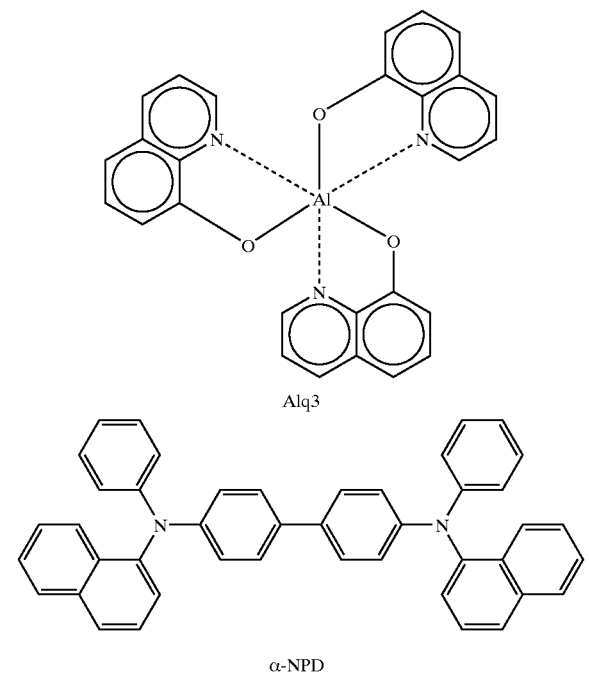

Alq3

α-NPD

-continued

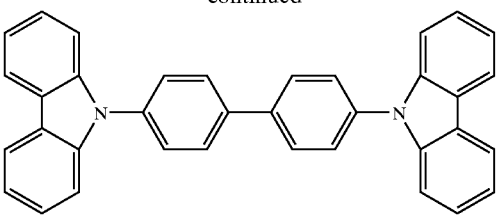
CBP

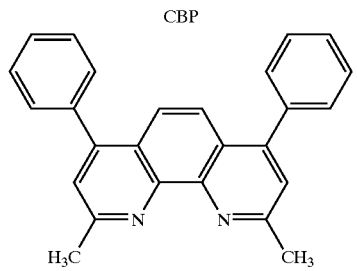
BCP

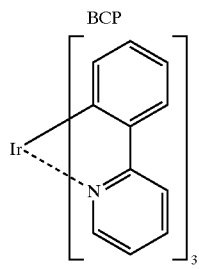
Ir(ppy)₃

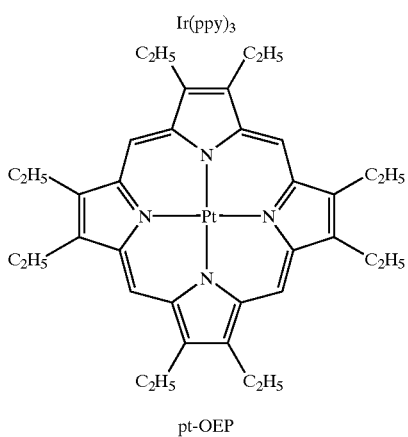
pt-OEP

Alq3: tris(8-hydroxyquinoline) aluminum (aluminum-quinolinol complex),

α-NPD: N4,N4'-di-naphthalene-1-yl-N4,N4'-diphenyl-biphenyl-4,4'-diamine (4,4'-bis[N-(1-naphthyl)-N-phenyl-amino]biphenyl), CBP: 4,4'-N,N'-dicarbazole-biphenyl, BCP: 2,9-dimethyl-4,7-diphenyl-1,10-phenanthroline, Ir(ppy)₃: fac tris(2-phenylpyridine)iridium (iridium-phenylpyridine complex), and PtEOP: 2,3,7,8,12,13,17,18-octaethyl-21H,23H-porphine platinum (platinum-octaethyl porphine complex).

The phosphorescence (luminescence) material used in the luminescence layer 12 has attracted notice. This is because the phosphorescence material is expected to provide a higher luminescence efficiency in principle.

More specifically, in the case of the phosphorescence material, excitons produced by recombination of carriers comprise singlet excitons and triplet excitons presented in a ratio of 1:3. For this reason, when fluorescence caused during the transition from the singlet excited state to the ground state is utilized, a resultant luminescence efficiency is 25% (as upper limit) based on all the produced excitons in principle.

On the other hand, in the case of utilizing phosphorescence caused during transition from the triplet excited state, a resultant luminescence efficiency is expected to be at least three times that of the case of fluorescence in principle. In addition thereto, if intersystem crossing from the singlet excited state (higher energy level) to the triplet excited state is taken into consideration, the luminescence efficiency of phosphorescence can be expected to be 100% (four times that of fluorescence) in principle.

The use of phosphorescence based on transition from the triplet excited state has also been proposed in, e.g., Japanese Laid-Open Patent Application (JP-A) 11-329739, JP-A 11-256148 and JP-A 8-319482.

However, the above-mentioned organic EL devices utilizing phosphorescence have accompanied with a problem of luminescent deterioration particularly in an energized state.

The reason for luminescent deterioration has not been clarified as yet but may be attributable to such a phenomenon that the life of triplet exciton is generally longer than that of singlet exciton by at least three digits, so that molecule is placed in a higher-energy state for a long period to cause reaction with ambient substance, formation of exciplex or excimer, change in minute molecular structure, structural change of ambient substance, etc.

Accordingly, the (electro)phosphorescence EL device is expected to provide a higher luminescence efficiency as described above, while the EL device is required to suppress or minimize the luminescent deterioration in energized state. Further, a luminescence center material for the EL device is required to allow high-efficiency luminescence and exhibit a good stability.

SUMMARY OF THE INVENTION

An object of the present invention is to provide a luminescence device capable of providing a high-efficiency luminescent state at a high brightness (or luminance) for a long period while minimizing the deterioration in luminescence in energized state.

Another object of the present invention is to provide a display apparatus including the luminescence device.

A further object of the present invention is to provide a metal coordination compound as a luminescence center material suitable for an organic layer for the luminescence device.

According to the present invention, there is provided a metal coordination compound (metal complex), particularly an iridium complex, characterized by having at least one aromatic substituent. More specifically, there is provided a metal coordination compound represented by formula (1) below:

$$ML_mL'_n \qquad (1),$$

wherein M is a metal atom of Ir, Pt, Rh or Pd; L and L' are mutually different bidentate ligands; m is 1, 2 or 3 and n is 0, 1 or 2 with the proviso that m+n is 2 or 3; a partial structure ML$_m$ is represented by formula (2) shown below and a partial structure ML'$_n$ is represented by formula (3) or (4) shown below:

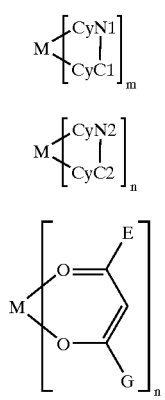

(2)
(3)
(4)

wherein CyN1 and CyN2 are each cyclic group capable of having a substituent, including a nitrogen atom and bonded to the metal atom M via the nitrogen atom; CyC1 and CyC2 are each cyclic group capable of having a substituent, including a carbon atom and bonded to the metal atom M via the carbon atom with the proviso that the cyclic group CyN1 and the cyclic group CyC1 are bonded to each other via a covalent bond and the cyclic group CyN2 and the cyclic group CyC2 are bonded to each other via a covalent bond;

the optional substituent of the cyclic groups is selected from a halogen atom, cyano group, a nitro group, a trialkylsilyl group of which the alkyl groups are independently a linear or branched alkyl group having 1 to 8 carbon atoms, a linear or branched alkyl group having 1 to 20 carbon atoms of which the alkyl group can include one or non-neighboring two or more methylene groups that can be replaced with —O—, —S—, —CO—, —CO—O—, —O—CO—, —CH═CH— or —C≡C—, and the alkyl group can include a hydrogen atom that can be optionally replaced with a fluorine atom; or an aromatic group capable of having a substituent which is selected from an aromatic group capable of having a substituent (that is a halogen atom, a cyano atom, a nitro atom, a linear or branched alkyl group having 1 to 20 carbon atoms of which the alkyl group can include one or non-neighboring two or more methylene groups that can be replaced with —O—, —S—, —CO—, —CO—O—, —O—CO—, —CH═CH— or —C≡C—, and the alkyl group can include a hydrogen atom that can be optionally replaced with a fluorine atom), a halogen atom, a cyano atom, a nitro atom, and a linear or branched alkyl group having 1 to 20 carbon atoms (of which the alkyl group can include one or non-neighboring two or more methylene groups that can be replaced with —O—, —S—, —CO—, —CO—O—, —O—CO—, —CH═CH— or —C≡C—, and the alkyl group can include a hydrogen atom that can be optionally replaced with a fluorine atom);

E and G are independently a linear or branched alkyl group having 1 to 20 carbon atoms of which the alkyl group can include a hydrogen atom that can be optionally replaced with a fluorine atom, or an aromatic group capable of having a substituent (that is a halogen atom, a cyano atom, a nitro atom, a trialkylsilyl group of which the alkyl groups are independently a linear or branched alkyl group having 1–8 carbon atoms, a linear or branched alkyl group having 1 to 20 carbon atoms of which the alkyl group can include one or non-neighboring two or more methylene groups that can be replaced with —O—, —S—, —CO—, —CO—O—, —O—CO—, —CH═CH— or —C≡C—, and the alkyl group can include a hydrogen atom that can be optionally replaced with a fluorine atom; and the cyclic groups CyN1, CyN2, CyC1 and CyC2 have at least one aromatic substituent capable of having a substituent which is selected from an aromatic group capable of having a substituent (that is a halogen atom, a cyano atom, a nitro atom, a linear or branched alkyl group having 1 to 20 carbon atoms of which the alkyl group can include one or non-neighboring two or more methylene groups that can be replaced with —O—, —S—, —CO—, —CO—O—, —O—CO—, —CH═CH— or —C≡C—, and the alkyl group can include a hydrogen atom that can be optionally replaced with a fluorine atom), a halogen atom, a cyano atom, a nitro atom, a linear or branched alkyl group having 1 to 20 carbon atoms of which the alkyl group can include one or non-neighboring two or more methylene groups that can be replaced with —O—, —S—, —CO—, —CO—O—, —O—CO—, —CH═CH— or —C≡C—, and the alkyl group can include a hydrogen atom that can be optionally replaced with a fluorine atom).

In the formula (1), M may preferably be Ir as described above, and n may preferably be 0.

In the formula (2), CyN1 and CyC1 may preferably be any one of the following combinations:

| CyN1 | CyC1 |
| --- | --- |
| pyridyl | naphthyl |
| pyridyl | thienyl |
| pyridyl | benzothienyl |

The present invention also provides an electroluminescence device, comprising: a pair of electrodes disposed on a substrate, and a luminescence unit comprising at least one organic compound disposed between the electrodes, wherein the organic compound comprises a metal coordination compound represented by the above-mentioned formula (1).

In the electroluminescence device, a voltage is applied between the electrodes to emit light.

In a preferred embodiment of the electroluminescence device, a voltage is applied between the electrodes to emit phosphorescence.

The present invention further provides a picture display apparatus, comprising an electroluminescence device described above and a means for supplying electric signals to the electroluminescence device.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 3A, 3B and 3C show device performances of a luminescence device used in Example 9 appearing hereinafter, wherein FIG. 3A shows an electric field strength-current density curve, FIG. 3B shows an electric field strength-luminance curve, and FIG. 3C shows a luminescence spectrum under application of a voltage of 10 volts.

DETAILED DESCRIPTION OF THE INVENTION

Figure 1A:
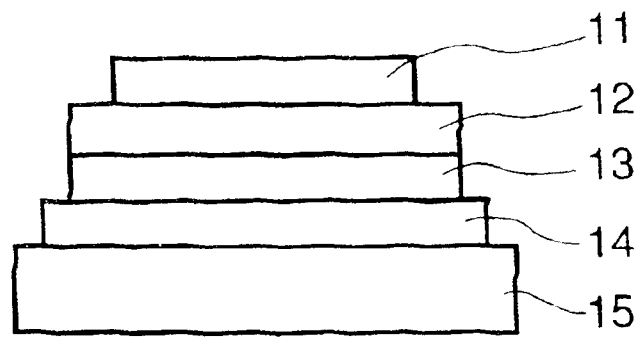
FIGS. 1A, 1B and 1C illustrate embodiments of the luminescence device according to the present invention, respectively.

In the case where the luminescence layer comprises a host material having a carrier-transporting function and a phosphorescent guest material, a process of phosphorescence via triplet excitons may include unit processes as follows:
1. transportation of electrons and holes within a luminescence layer,
2. formation of host excitons,
3. excitation energy transfer between host molecules,
4. excitation energy transfer from the host to the guest,
5. formation of guest triplet excitons, and
6. transition of the guest triplet excitons to the ground state and phosphorescence.

Desirable energy transfer in each unit process and luminescence are caused in competition with various energy deactivation processes.

Needless to say, a luminescence efficiency of an organic luminescence device is increased by increasing the luminescence quantum yield of a luminescence center material. In addition thereto, an efficient energy transfer between host material molecules and/or between host material molecule and guest material molecule is also an important factor.

Further, the above-described luminescent deterioration in energized state may presumably relate to the luminescent center material per se or an environmental change thereof by its ambient molecular structure.

For this reason, our research group has extensively investigated an effect of use of the metal coordination compound of formula (1) as the luminescent center material and as a result, has found that the metal coordination compound of formula (1) allows a high-efficiency luminescence with a high brightness (luminance) for a long period, and less deterioration in energized state.

The metal coordination compound represented by the above formula (1) according to the present invention causes phosphorescence (luminescence) and its lowest excited state is believed to be an MLCT* (metal-to-ligand charge transfer) excited state or π-π* excited state in a triplet state. The phosphorescent emission of light (phosphorescence) is caused at the time of transition from such a state to the ground state.

The metal coordination compound of formula (1) according to the present invention has been found to provide a higher phosphorescence (quantum) yield of 0.05–0.9 and a shorter phosphorescence life of 1–40 μsec, as a result of our luminescence experiment based on photoluminescence by photo-excitation.

The shorter phosphorescence life is necessary to provide a resultant EL device with a higher luminescence efficiency. This is because the longer phosphorescence life increases molecules placed in their triplet excited state which is a waiting state for phosphorescence, thus lowering the resultant luminescence efficiency particularly at a higher current density. Further, an emission wavelength can be controlled by changing appropriately substituents R1 to T6 and species of aromatic group of the metal coordination compound of the formula (1).

Also from these viewpoints, the metal coordination compound of formula (1) according to the present invention is a suitable luminescent material for an EL device with a higher phosphorescence yield and a shorter phosphorescence life.

Particularly, by providing an aromatic group as a substituent (i.e., aromatic substituent) of the metal coordination compound of the formula (1), the resultant substituent has π-electron system extended to the outside of the metal coordination compound molecules, thus facilitating energy transfer from a host material and assisting electron/hole transport functions to result in an improved carrier transport performance. Further, in the present invention, the metal coordination compound of the formula (1) may preferably have the cyclic group CyN1 and/or CyN2 having pyridine structure, a pyridine derivative whereon one of CH groups is substituted with N atom, and five-membered ring structures containing nitrogen atom and/or sulfur atom. By these partial structures, the resultant metal coordination compound of the formula (1) can be synthesized with a high yield and an excellent stability necessary for the luminescence material.

In addition, as substantiated in Examples appearing hereinafter, it has been confirmed that the metal coordination compound of the formula (1) also exhibited an excellent stability in a durability test by continuous current passage. This may be attributable to a controlled intermolecular interaction of the metal coordination compound of the formula (1) with the host material by introducing the aromatic substituent characterizing the metal coordination compound of the present invention into the metal coordination compound thereby to change an intermolecular interaction. As a result, it becomes possible to suppress formation of exciton associates leading to thermal deactivation, thus also reducing quenching process to improve phosphorescence yield and device characteristics.

In the present invention, as the aromatic substituent for the metal coordination compound of the formula (1), it is preferred to use an aromatic group selected from the group consisting of those (sPh to sPe) shown hereinafter.

In the present invention, the luminescence device may preferably include the organic layer comprising the above-mentioned metal coordination compound between a pair of oppositely disposed electrodes comprising a transparent electrode (anode) and a metal electrode (cathode) which are supplied with a voltage to cause luminescence, thus constituting an electric-field luminescence device.

Figure 1B:
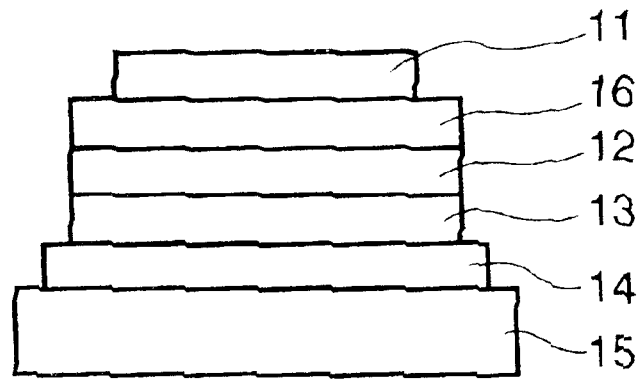
Figure 1C:
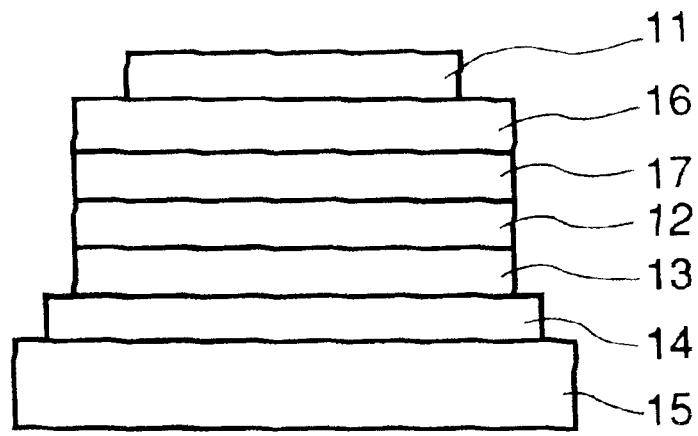

The luminescence device of the present invention has a layer structure shown in FIGS. 1A to 1C as specifically described above.

By the use of the metal coordination compound of formula (1) of the present invention, the resultant luminescence device has a high luminescence efficiency as described above.

The luminescence device according to the present invention may be applicable to devices required to allow energy saving and high luminance, such as those for display apparatus and illumination apparatus, a light source for printers, and backlight (unit) for a liquid crystal display apparatus. Specifically, in the case of using the luminescence device of the present invention in the display apparatus, it is possible to provide a flat panel display apparatus capable of exhibiting an excellent energy saving performance, a high visibility and a good lightweight property. With respect to the light source, it becomes possible to replace a laser light source of laser beam printer currently used widely with the luminescence device according to the present invention. Further, when the luminescence device of the present invention is arranged in independently addressable arrays as an exposure means for effecting desired exposure of light to a photosensitive drum for forming an image, it becomes possible to considerably reducing the volume (size) of image forming apparatus. With respect to the illumination apparatus and backlight (unit), the resultant apparatus (unit) using the luminescence device of the present invention is expected to have an energy saving effect.

For the application to a display, a drive system using a thin-film transistor (TFT) drive circuit according to an active matrix-scheme may be used. Hereinbelow, an embodiment of using a device of the present invention in combination with a active matrix substrate is briefly described with reference to FIG. 2.

Figure 2:
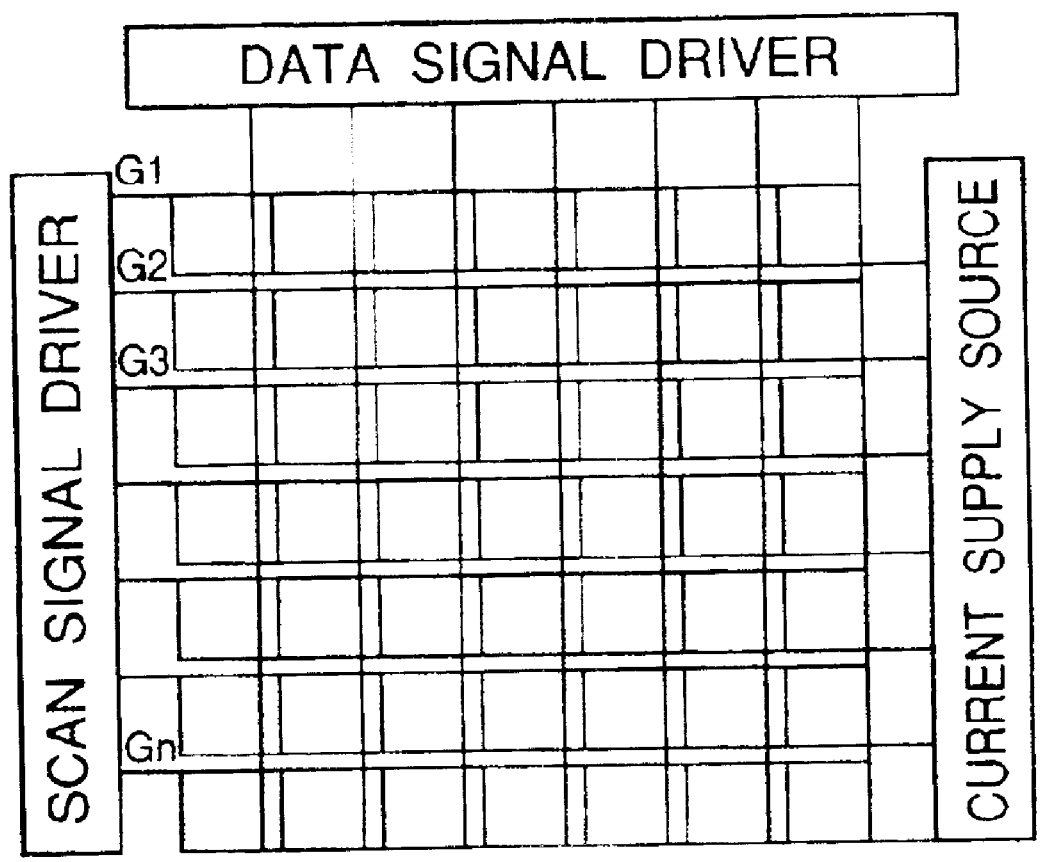
FIG. 2 schematically illustrates a panel structure including an EL device and drive means.

FIG. 2 illustrates an embodiment of panel structure comprising an EL device and drive means. The panel is provided with a scanning signal driver, a data signal driver and a current supply source which are connected to gate selection lines, data signal lines and current supply lines, respectively. At each intersection of the gate selection lines and the data signal lines, a display pixel electrode is disposed. The scanning signal drive sequentially selects the gate selection lines G1, G2, G3 . . . Gn, and in synchronism herewith, picture signals are supplied from the data signal driver to display a picture (image).

By driving a display panel including a luminescence layer comprising a luminescence material of the present invention, it becomes possible to provide a display which exhibits a good picture quality and is stable even for a long period display.

Some synthetic paths for providing a metal coordination compound represented by the above-mentioned formula (1) are illustrated below with reference to an iridium coordination compound (m+n=3) for example:

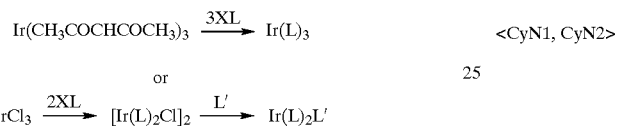

Other metal coordination compound (M=Pt, Rh and Pd) can also be synthesized in a similar manner.

Some specific structural examples of metal coordination compounds used in the present invention are shown in Tables 1 to Tables 17 appearing hereinafter, which are however only representative examples and are not exhaustive. Ph to sPe for CyN1, CyN2, CyC1, CyC2 and aromatic substituent(s) shown in Tables 1 to 17 represent partial structures shown below.

<CyC1, CyC2>

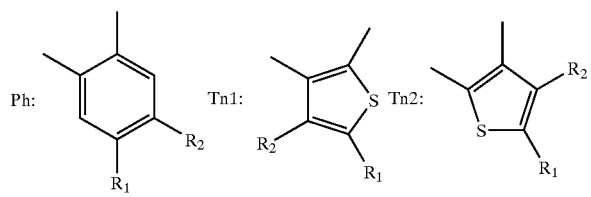

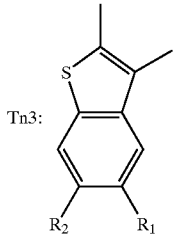

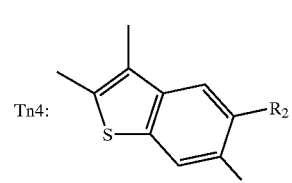

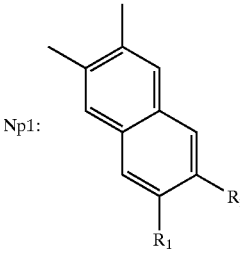

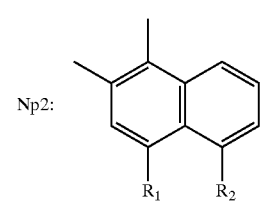

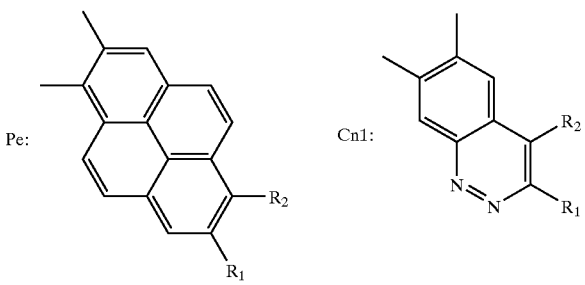

<CyN1, CyN2>

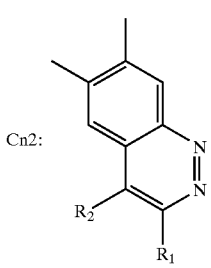

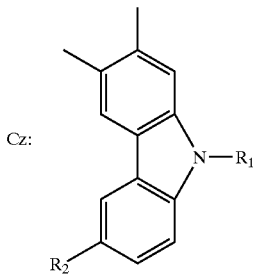

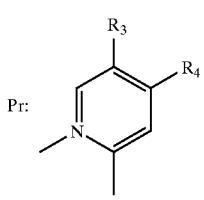

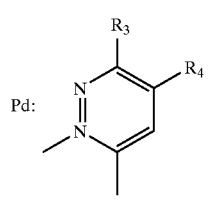

<Aromatic substituent>

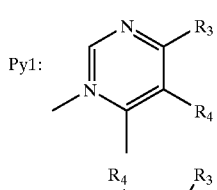

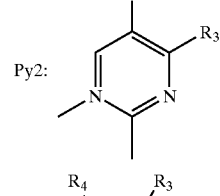

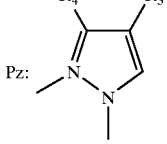

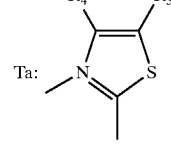

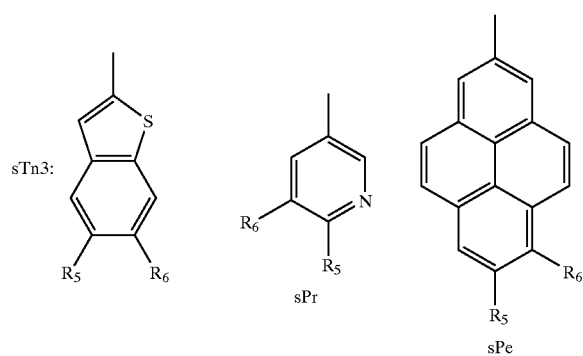

TABLE 1

| No | M | m | CyN1 | CyC1 | R1 | R2 | R3 | R4 |
|---|---|---|---|---|---|---|---|---|
| 1 | Ir | 3 | Pr | Ph | H | H | sPh | H |
| 2 | Ir | 3 | Pr | Ph | H | H | sNp1 | H |
| 3 | Ir | 3 | Pr | Ph | H | H | sNp2 | H |
| 4 | Ir | 3 | Pr | Ph | H | H | sTn1 | H |
| 5 | Ir | 3 | Pr | Ph | H | H | sTn3 | H |
| 6 | Ir | 3 | Pr | Ph | H | H | sPr | H |
| 7 | Ir | 3 | Pr | Ph | H | H | sPe | H |
| 8 | Ir | 3 | Pr | Tn1 | H | H | sPh | H |
| 9 | Ir | 3 | Pr | Tn1 | H | H | sNp1 | H |
| 10 | Ir | 3 | Pr | Tn1 | H | H | sNp2 | H |
| 11 | Ir | 3 | Pr | Tn1 | H | H | sTn1 | H |
| 12 | Ir | 3 | Pr | Tn1 | H | H | sTn3 | H |
| 13 | Ir | 3 | Pr | Tn1 | H | H | sPr | H |
| 14 | Ir | 3 | Pr | Tn1 | H | H | sPe | H |
| 15 | Ir | 3 | Pr | Tn2 | H | H | sPh | H |
| 16 | Ir | 3 | Pr | Tn2 | H | H | sNp1 | H |
| 17 | Ir | 3 | Pr | Tn2 | H | H | sNp2 | H |
| 18 | Ir | 3 | Pr | Tn2 | H | H | sTn1 | H |
| 19 | Ir | 3 | Pr | Tn2 | H | H | sTn3 | H |
| 20 | Ir | 3 | Pr | Tn2 | H | H | sPr | H |
| 21 | Ir | 3 | Pr | Tn2 | H | H | sPe | H |
| 22 | Ir | 3 | Pr | Tn3 | H | H | sPh | H |
| 23 | Ir | 3 | Pr | Tn3 | H | H | sNp1 | H |
| 24 | Ir | 3 | Pr | Tn3 | H | H | sNp2 | H |
| 25 | Ir | 3 | Pr | Tn3 | H | H | sTn1 | H |
| 26 | Ir | 3 | Pr | Tn3 | H | H | sTn3 | H |
| 27 | Ir | 3 | Pr | Tn3 | H | H | sPr | H |
| 28 | Ir | 3 | Pr | Tn3 | H | H | sPe | H |
| 29 | Ir | 3 | Pr | Tn4 | H | H | sPh | H |
| 30 | Ir | 3 | Pr | Tn4 | H | H | sNp1 | H |
| 31 | Ir | 3 | Pr | Tn4 | H | H | sNp2 | H |
| 32 | Ir | 3 | Pr | Tn4 | H | H | sTn1 | H |
| 33 | Ir | 3 | Pr | Tn4 | H | H | sTn3 | H |
| 34 | Ir | 3 | Pr | Tn4 | H | H | sPr | H |
| 35 | Ir | 3 | Pr | Tn4 | H | H | sPe | H |
| 36 | Ir | 3 | Pr | Np1 | H | H | sPh | H |
| 37 | Ir | 3 | Pr | Np1 | H | H | sNp1 | H |
| 38 | Ir | 3 | Pr | Np1 | H | H | sNp2 | H |
| 39 | Ir | 3 | Pr | Np1 | H | H | sTn1 | H |
| 40 | Ir | 3 | Pr | Np1 | H | H | sTn3 | H |
| 41 | Ir | 3 | Pr | Np1 | H | H | sPr | H |
| 42 | Ir | 3 | Pr | Np1 | H | H | sPe | H |
| 43 | Ir | 3 | Pr | Np2 | H | H | H | sPh |
| 44 | Ir | 3 | Pr | Np2 | H | H | sNp1 | H |
| 45 | Ir | 3 | Pr | Np2 | H | H | sNp2 | H |
| 46 | Ir | 3 | Pr | Np2 | H | H | sTn1 | H |
| 47 | Ir | 3 | Pr | Np2 | H | H | sTn3 | H |
| 48 | Ir | 3 | Pr | Np2 | H | H | sPr | H |
| 49 | Ir | 3 | Pr | Np2 | H | H | sPe | H |
| 50 | Ir | 3 | Pr | Pe | H | H | sPh | H |
| 51 | Ir | 3 | Pr | Pe | H | H | sNp1 | H |
| 52 | Ir | 3 | Pr | Pe | H | H | sNp2 | H |

TABLE 2

| No | M | m | CyN1 | CyC1 | R1 | R2 | R3 | R4 |
|---|---|---|---|---|---|---|---|---|
| 53 | Ir | 3 | Pr | Pe | H | H | sTn1 | H |
| 54 | Ir | 3 | Pr | Pe | H | H | sTn3 | H |
| 55 | Ir | 3 | Pr | Pe | H | H | sPr | H |
| 56 | Ir | 3 | Pr | Pe | H | H | sPe | H |
| 57 | Ir | 3 | Pr | Cn1 | H | H | sPh | H |
| 58 | Ir | 3 | Pr | Cn1 | H | H | sNp1 | H |
| 59 | Ir | 3 | Pr | Cn1 | H | H | sNp2 | H |
| 60 | Ir | 3 | Pr | Cn1 | H | H | sTn1 | H |
| 61 | Ir | 3 | Pr | Cn1 | H | H | sTn3 | H |
| 62 | Ir | 3 | Pr | Cn1 | H | H | sPr | H |
| 63 | Ir | 3 | Pr | Cn1 | H | H | sPe | H |
| 64 | Ir | 3 | Pr | Cn2 | H | H | sPh | H |
| 65 | Ir | 3 | Pr | Cn2 | H | H | sNp1 | H |
| 66 | Ir | 3 | Pr | Cn2 | H | H | sNp2 | H |
| 67 | Ir | 3 | Pr | Cn2 | H | H | sTn1 | H |
| 68 | Ir | 3 | Pr | Cn2 | H | H | sTn3 | H |
| 69 | Ir | 3 | Pr | Cn2 | H | H | sPr | H |
| 70 | Ir | 3 | Pr | Cn2 | H | H | sPe | H |
| 71 | Ir | 3 | Pr | Cz | H | H | sPh | H |
| 72 | Ir | 3 | Pr | Cz | H | H | sNp1 | H |
| 73 | Ir | 3 | Pr | Cz | H | H | sNp2 | H |
| 74 | Ir | 3 | Pr | Cz | H | H | sTn1 | H |
| 75 | Ir | 3 | Pr | Cz | H | H | sTn3 | H |
| 76 | Ir | 3 | Pr | Cz | H | H | sPr | H |
| 77 | Ir | 3 | Pr | Cz | H | H | sPe | H |
| 78 | Ir | 3 | Pd | Ph | H | H | sPh | H |
| 79 | Ir | 3 | Pd | Ph | H | H | sNp1 | H |
| 80 | Ir | 3 | Pd | Ph | H | H | sNp2 | H |
| 81 | Ir | 3 | Pd | Ph | H | H | sTn1 | H |
| 82 | Ir | 3 | Pd | Ph | H | H | sTn3 | H |
| 83 | Ir | 3 | Pd | Ph | H | H | sPr | H |
| 84 | Ir | 3 | Pd | Ph | H | H | sPe | H |
| 85 | Ir | 3 | Pd | Tn1 | H | H | sPh | H |
| 86 | Ir | 3 | Pd | Tn1 | H | H | sNp1 | H |
| 87 | Ir | 3 | Pd | Tn1 | H | H | sNp2 | H |
| 88 | Ir | 3 | Pd | Tn1 | H | H | sTn1 | H |
| 89 | Ir | 3 | Pd | Tn1 | H | H | sTn3 | H |
| 90 | Ir | 3 | Pd | Tn1 | H | H | sPr | H |
| 91 | Ir | 3 | Pd | Tn1 | H | H | sPe | H |
| 92 | Ir | 3 | Pd | Tn2 | H | H | sPh | H |
| 93 | Ir | 3 | Pd | Tn2 | H | H | sNp1 | H |
| 94 | Ir | 3 | Pd | Tn2 | H | H | sNp2 | H |
| 95 | Ir | 3 | Pd | Tn2 | H | H | sTn1 | H |
| 96 | Ir | 3 | Pd | Tn2 | H | H | sTn3 | H |
| 97 | Ir | 3 | Pd | Tn2 | H | H | sPr | H |
| 98 | Ir | 3 | Pd | Tn2 | H | H | sPe | H |
| 99 | Ir | 3 | Pd | Tn3 | H | H | sPh | H |
| 100 | Ir | 3 | Pd | Tn3 | H | H | sNp1 | H |
| 101 | Ir | 3 | Pd | Tn3 | H | H | sNp2 | H |
| 102 | Ir | 3 | Pd | Tn3 | H | H | sTn1 | H |
| 103 | Ir | 3 | Pd | Tn3 | H | H | sTn3 | H |
| 104 | Ir | 3 | Pd | Tn3 | H | H | sPr | H |

TABLE 3

| No | M | m | CyN1 | CyC1 | R1 | R2 | R3 | R4 |
|---|---|---|---|---|---|---|---|---|
| 105 | Ir | 3 | Pd | Tn3 | H | H | sPe | H |
| 106 | Ir | 3 | Pd | Tn4 | H | H | sPh | H |
| 107 | Ir | 3 | Pd | Tn4 | H | H | sNp1 | H |
| 108 | Ir | 3 | Pd | Tn4 | H | H | sNp2 | H |
| 109 | Ir | 3 | Pd | Tn4 | H | H | sTn1 | H |
| 110 | Ir | 3 | Pd | Tn4 | H | H | sTn3 | H |
| 111 | Ir | 3 | Pd | Tn4 | H | H | sPr | H |
| 112 | Ir | 3 | Pd | Tn4 | H | H | sPe | H |
| 113 | Ir | 3 | Pd | Np1 | H | H | sPh | H |
| 114 | Ir | 3 | Pd | Np1 | H | H | sNp1 | H |
| 115 | Ir | 3 | Pd | Np1 | H | H | sNp2 | H |
| 116 | Ir | 3 | Pd | Np1 | H | H | sTn1 | H |
| 117 | Ir | 3 | Pd | Np1 | H | H | sTn3 | H |
| 118 | Ir | 3 | Pd | Np1 | H | H | sPr | H |
| 119 | Ir | 3 | Pd | Np1 | H | H | sPe | H |
| 120 | Ir | 3 | Pd | Np2 | H | H | sPh | H |
| 121 | Ir | 3 | Pd | Np2 | H | H | sNp1 | H |

TABLE 3-continued

| No | M | m | CyN1 | CyC1 | R1 | R2 | R3 | R4 |
|---|---|---|---|---|---|---|---|---|
| 122 | Ir | 3 | Pd | Np2 | H | H | sNp2 | H |
| 123 | Ir | 3 | Pd | Np2 | H | H | sTn1 | H |
| 124 | Ir | 3 | Pd | Np2 | H | H | sTn3 | H |
| 125 | Ir | 3 | Pd | Np2 | H | H | sPr | H |
| 126 | Ir | 3 | Pd | Np2 | H | H | sPe | H |
| 127 | Ir | 3 | Pd | Pe | H | H | sPh | H |
| 128 | Ir | 3 | Pd | Pe | H | H | sNp1 | H |
| 129 | Ir | 3 | Pd | Pe | H | H | sNp2 | H |
| 130 | Ir | 3 | Pd | Pe | H | H | sTn1 | H |
| 131 | Ir | 3 | Pd | Pe | H | H | sTn3 | H |
| 132 | Ir | 3 | Pd | Pe | H | H | sPr | H |
| 133 | Ir | 3 | Pd | Pe | H | H | sPe | H |
| 134 | Ir | 3 | Pd | Cn1 | H | H | sPh | H |
| 135 | Ir | 3 | Pd | Cn1 | H | H | sNp1 | H |
| 136 | Ir | 3 | Pd | Cn1 | H | H | sNp2 | H |
| 137 | Ir | 3 | Pd | Cn1 | H | H | sTn1 | H |
| 138 | Ir | 3 | Pd | Cn1 | H | H | sTn3 | H |
| 139 | Ir | 3 | Pd | Cn1 | H | H | sPr | H |
| 140 | Ir | 3 | Pd | Cn1 | H | H | sPe | H |
| 141 | Ir | 3 | Pd | Cn2 | H | H | sPh | H |
| 142 | Ir | 3 | Pd | Cn2 | H | H | sNp1 | H |
| 143 | Ir | 3 | Pd | Cn2 | H | H | sNp2 | H |
| 144 | Ir | 3 | Pd | Cn2 | H | H | sTn1 | H |
| 145 | Ir | 3 | Pd | Cn2 | H | H | sTn3 | H |
| 146 | Ir | 3 | Pd | Cn2 | H | H | sPr | H |
| 147 | Ir | 3 | Pd | Cn2 | H | H | sPe | H |
| 148 | Ir | 3 | Pd | Cz | H | H | sPh | H |
| 149 | Ir | 3 | Pd | Cz | H | H | sNp1 | H |
| 150 | Ir | 3 | Pd | Cz | H | H | sNp2 | H |
| 151 | Ir | 3 | Pd | Cz | H | H | sTn1 | H |
| 152 | Ir | 3 | Pd | Cz | H | H | sTn3 | H |
| 153 | Ir | 3 | Pd | Cz | H | H | sPr | H |
| 154 | Ir | 3 | Pd | Cz | H | H | sPe | H |
| 155 | Ir | 3 | Pz | Ph | H | H | sPh | H |
| 156 | Ir | 3 | Pd | Ph | H | H | sNp1 | H |

TABLE 4

| No | M | m | CyN1 | CyC1 | R1 | R2 | R3 | R4 |
|---|---|---|---|---|---|---|---|---|
| 157 | Ir | 3 | Pd | Ph | H | H | sNp2 | H |
| 158 | Ir | 3 | Pd | Ph | H | H | sTn1 | H |
| 159 | Ir | 3 | Pd | Ph | H | H | sTn3 | H |
| 160 | Ir | 3 | Pd | Ph | H | H | sPr | H |
| 161 | Ir | 3 | Pd | Ph | H | H | sPe | H |
| 162 | Ir | 3 | Pd | Tn1 | H | H | sPh | H |
| 163 | Ir | 3 | Pd | Tn1 | H | H | sNp1 | H |
| 164 | Ir | 3 | Pd | Tn1 | H | H | sNp2 | H |
| 165 | Ir | 3 | Pd | Tn1 | H | H | sTn1 | H |
| 166 | Ir | 3 | Pd | Tn1 | H | H | sTn3 | H |
| 167 | Ir | 3 | Pd | Tn1 | H | H | sPr | H |
| 168 | Ir | 3 | Pd | Tn1 | H | H | sPe | H |
| 169 | Ir | 3 | Pd | Tn2 | H | H | sPh | H |
| 170 | Ir | 3 | Pd | Tn2 | H | H | sNp1 | H |
| 171 | Ir | 3 | Pd | Tn2 | H | H | sNp2 | H |
| 172 | Ir | 3 | Pd | Tn2 | H | H | sTn1 | H |
| 173 | Ir | 3 | Pd | Tn2 | H | H | sTn3 | H |
| 174 | Ir | 3 | Pd | Tn2 | H | H | sPr | H |
| 175 | Ir | 3 | Pd | Tn2 | H | H | sPe | H |
| 176 | Ir | 3 | Pd | Tn3 | H | H | sPh | H |
| 177 | Ir | 3 | Pd | Tn3 | H | H | sNp1 | H |
| 178 | Ir | 3 | Pd | Tn3 | H | H | sNp2 | H |
| 179 | Ir | 3 | Pd | Tn3 | H | H | sTn1 | H |
| 180 | Ir | 3 | Pd | Tn3 | H | H | sTn3 | H |
| 181 | Ir | 3 | Pd | Tn3 | H | H | sPr | H |
| 182 | Ir | 3 | Pd | Tn3 | H | H | sPe | H |
| 183 | Ir | 3 | Pd | Tn4 | H | H | sPh | H |
| 184 | Ir | 3 | Pd | Tn4 | H | H | sNp1 | H |
| 185 | Ir | 3 | Pd | Tn4 | H | H | sNp2 | H |
| 186 | Ir | 3 | Pd | Tn4 | H | H | sTn1 | H |
| 187 | Ir | 3 | Pd | Tn4 | H | H | sTn3 | H |
| 188 | Ir | 3 | Pd | Tn4 | H | H | sPr | H |
| 189 | Ir | 3 | Pd | Tn4 | H | H | sPe | H |
| 190 | Ir | 3 | Pd | Np1 | H | H | sPh | H |

TABLE 4-continued

| No | M | m | CyN1 | CyC1 | R1 | R2 | R3 | R4 |
|---|---|---|---|---|---|---|---|---|
| 191 | Ir | 3 | Pd | Np1 | H | H | sNp1 | H |
| 192 | Ir | 3 | Pd | Np1 | H | H | sNp2 | H |
| 193 | Ir | 3 | Pd | Np1 | H | H | sTn1 | H |
| 194 | Ir | 3 | Pd | Np1 | H | H | sTn3 | H |
| 195 | Ir | 3 | Pd | Np1 | H | H | sPr | H |
| 196 | Ir | 3 | Pd | Np1 | H | H | sPe | H |
| 197 | Ir | 3 | Pd | Np2 | H | H | sPh | H |
| 198 | Ir | 3 | Pd | Np2 | H | H | sNp1 | H |
| 199 | Ir | 3 | Pd | Np2 | H | H | sNp2 | H |
| 200 | Ir | 3 | Pd | Np2 | H | H | sTn1 | H |
| 201 | Ir | 3 | Pd | Np2 | H | H | sTn3 | H |
| 202 | Ir | 3 | Pd | Np2 | H | H | sPr | H |
| 203 | Ir | 3 | Pd | Np2 | H | H | sPe | H |
| 204 | Ir | 3 | Pd | Pe | H | H | sPh | H |
| 205 | Ir | 3 | Pd | Pe | H | H | sNp1 | H |
| 206 | Ir | 3 | Pd | Pe | H | H | sNp2 | H |
| 207 | Ir | 3 | Pd | Pe | H | H | sTn1 | H |
| 208 | Ir | 3 | Pd | Pe | H | H | sTn3 | H |

TABLE 5

| No | M | m | CyN1 | CyC1 | R1 | R2 | R3 | R4 |
|---|---|---|---|---|---|---|---|---|
| 209 | Ir | 3 | Pd | Pe | H | H | sPr | H |
| 210 | Ir | 3 | Pd | Pe | H | H | sPe | H |
| 211 | Ir | 3 | Pd | Cn1 | H | H | sPh | H |
| 212 | Ir | 3 | Pd | Cn1 | H | H | sNp1 | H |
| 213 | Ir | 3 | Pd | Cn1 | H | H | sNp2 | H |
| 214 | Ir | 3 | Pd | Cn1 | H | H | sTn1 | H |
| 215 | Ir | 3 | Pd | Cn1 | H | H | sTn3 | H |
| 216 | Ir | 3 | Pd | Cn1 | H | H | sPr | H |
| 217 | Ir | 3 | Pd | Cn1 | H | H | sPe | H |
| 218 | Ir | 3 | Pd | Cn2 | H | H | sPh | H |
| 219 | Ir | 3 | Pd | Cn2 | H | H | sNp1 | H |
| 220 | Ir | 3 | Pd | Cn2 | H | H | sNp2 | H |
| 221 | Ir | 3 | Pd | Cn2 | H | H | sTn1 | H |
| 222 | Ir | 3 | Pd | Cn2 | H | H | sTn3 | H |
| 223 | Ir | 3 | Pd | Cn2 | H | H | sPr | H |
| 224 | Ir | 3 | Pd | Cn2 | H | H | sPe | H |
| 225 | Ir | 3 | Pd | Cz | H | H | sPh | H |
| 226 | Ir | 3 | Pd | Cz | H | H | sNp1 | H |
| 227 | Ir | 3 | Pd | Cz | H | H | sNp2 | H |
| 228 | Ir | 3 | Pd | Cz | H | H | sTn1 | H |
| 229 | Ir | 3 | Pd | Cz | H | H | sTn3 | H |
| 230 | Ir | 3 | Pd | Cz | H | H | sPr | H |
| 231 | Ir | 3 | Pd | Cz | H | H | sPe | H |
| 232 | Ir | 3 | Pz | Ph | H | H | sPh | H |
| 233 | Ir | 3 | Pz | Ph | H | H | sNp1 | H |
| 234 | Ir | 3 | Pz | Ph | H | H | sNp2 | H |
| 235 | Ir | 3 | Pz | Ph | H | H | sTn1 | H |
| 236 | Ir | 3 | Pz | Ph | H | H | sTn3 | H |
| 237 | Ir | 3 | Pz | Ph | H | H | sPr | H |
| 238 | Ir | 3 | Pz | Ph | H | H | sPe | H |
| 239 | Ir | 3 | Pz | Tn1 | H | H | sPh | H |
| 240 | Ir | 3 | Pz | Tn1 | H | H | sNp1 | H |
| 241 | Ir | 3 | Pz | Tn1 | H | H | sNp2 | H |
| 242 | Ir | 3 | Pz | Tn1 | H | H | sTn1 | H |
| 243 | Ir | 3 | Pz | Tn1 | H | H | sTn3 | H |
| 244 | Ir | 3 | Pz | Tn1 | H | H | sPr | H |
| 245 | Ir | 3 | Pz | Tn1 | H | H | sPe | H |
| 246 | Ir | 3 | Pz | Tn2 | H | H | sPh | H |
| 247 | Ir | 3 | Pz | Tn2 | H | H | sNp1 | H |
| 248 | Ir | 3 | Pz | Tn2 | H | H | sNp2 | H |
| 249 | Ir | 3 | Pz | Tn2 | H | H | sTn1 | H |
| 250 | Ir | 3 | Pz | Tn2 | H | H | sTn3 | H |
| 251 | Ir | 3 | Pz | Tn2 | H | H | sPr | H |
| 252 | Ir | 3 | Pz | Tn2 | H | H | sPe | H |
| 253 | Ir | 3 | Pz | Tn3 | H | H | sPh | H |
| 254 | Ir | 3 | Pz | Tn3 | H | H | sNp1 | H |
| 255 | Ir | 3 | Pz | Tn3 | H | H | sNp2 | H |
| 256 | Ir | 3 | Pz | Tn3 | H | H | sTn1 | H |
| 257 | Ir | 3 | Pz | Tn3 | H | H | sTn3 | H |
| 258 | Ir | 3 | Pz | Tn3 | H | H | sPr | H |
| 259 | Ir | 3 | Pz | Tn3 | H | H | sPe | H |

TABLE 5-continued

| No | M | m | CyN1 | CyC1 | R1 | R2 | R3 | R4 |
|---|---|---|---|---|---|---|---|---|
| 260 | Ir | 3 | Pz | Tn4 | H | H | sPh | H |

TABLE 6

| No | M | m | CyN1 | CyC1 | R1 | R2 | R3 | R4 |
|---|---|---|---|---|---|---|---|---|
| 261 | Ir | 3 | Pz | Tn4 | H | H | sNp1 | H |
| 262 | Ir | 3 | Pz | Tn4 | H | H | sNp2 | H |
| 263 | Ir | 3 | Pz | Tn4 | H | H | sTn1 | H |
| 264 | Ir | 3 | Pz | Tn4 | H | H | sTn3 | H |
| 265 | Ir | 3 | Pz | Tn4 | H | H | sPr | H |
| 266 | Ir | 3 | Pz | Tn4 | H | H | sPe | H |
| 267 | Ir | 3 | Pz | Np1 | H | H | sPh | H |
| 268 | Ir | 3 | Pz | Np1 | H | H | sNp1 | H |
| 269 | Ir | 3 | Pz | Np1 | H | H | sNp2 | H |
| 270 | Ir | 3 | Pz | Np1 | H | H | sTn1 | H |
| 271 | Ir | 3 | Pz | Np1 | H | H | sTn3 | H |
| 272 | Ir | 3 | Pz | Np1 | H | H | sPr | H |
| 273 | Ir | 3 | Pz | Np1 | H | H | sPe | H |
| 274 | Ir | 3 | Pz | Np2 | H | H | sPh | H |
| 275 | Ir | 3 | Pz | Np2 | H | H | sNp1 | H |
| 276 | Ir | 3 | Pz | Np2 | H | H | sNp2 | H |
| 277 | Ir | 3 | Pz | Np2 | H | H | sTn1 | H |
| 278 | Ir | 3 | Pz | Np2 | H | H | sTn3 | H |
| 279 | Ir | 3 | Pz | Np2 | H | H | sPr | H |
| 280 | Ir | 3 | Pz | Np2 | H | H | sPe | H |
| 281 | Ir | 3 | Pz | Pe | H | H | sPh | H |
| 282 | Ir | 3 | Pz | Pe | H | H | sNp1 | H |
| 283 | Ir | 3 | Pz | Pe | H | H | sNp2 | H |
| 284 | Ir | 3 | Pz | Pe | H | H | sTn1 | H |
| 285 | Ir | 3 | Pz | Pe | H | H | sTn3 | H |
| 286 | Ir | 3 | Pz | Pe | H | H | sPr | H |
| 287 | Ir | 3 | Pz | Pe | H | H | sPe | H |
| 288 | Ir | 3 | Pz | Cn1 | H | H | sPh | H |
| 289 | Ir | 3 | Pz | Cn1 | H | H | sNp1 | H |
| 290 | Ir | 3 | Pz | Cn1 | H | H | sNp2 | H |
| 291 | Ir | 3 | Pz | Cn1 | H | H | sTn1 | H |
| 292 | Ir | 3 | Pz | Cn1 | H | H | sTn3 | H |
| 293 | Ir | 3 | Pz | Cn1 | H | H | sPr | H |
| 294 | Ir | 3 | Pz | Cn1 | H | H | sPe | H |
| 295 | Ir | 3 | Pz | Cn2 | H | H | sPh | H |
| 296 | Ir | 3 | Pz | Cn2 | H | H | sNp1 | H |
| 297 | Ir | 3 | Pz | Cn2 | H | H | sNp2 | H |
| 298 | Ir | 3 | Pz | Cn2 | H | H | sTn1 | H |
| 299 | Ir | 3 | Pz | Cn2 | H | H | sTn3 | H |
| 300 | Ir | 3 | Pz | Cn2 | H | H | sPr | H |
| 301 | Ir | 3 | Pz | Cn2 | H | H | sPe | H |
| 302 | Ir | 3 | Pz | Cz | H | H | sPh | H |
| 303 | Ir | 3 | Pz | Cz | H | H | sNp1 | H |
| 304 | Ir | 3 | Pz | Cz | H | H | sNp2 | H |
| 305 | Ir | 3 | Pz | Cz | H | H | sTn1 | H |
| 306 | Ir | 3 | Pz | Cz | H | H | sTn3 | H |
| 307 | Ir | 3 | Pz | Cz | H | H | sPr | H |
| 308 | Ir | 3 | Pz | Cz | H | H | sPe | H |
| 309 | Ir | 3 | Py1 | Ph | H | H | sPh | H |
| 310 | Ir | 3 | Py1 | Ph | H | H | sNp1 | H |
| 311 | Ir | 3 | Py1 | Ph | H | H | sTn1 | H |
| 312 | Ir | 3 | Py1 | Ph | H | H | sTn3 | H |

TABLE 7

| No | M | m | CyN1 | CyC1 | R1 | R2 | R3 | R4 |
|---|---|---|---|---|---|---|---|---|
| 313 | Ir | 3 | Py1 | Tn1 | H | H | sPh | H |
| 314 | Ir | 3 | Py1 | Tn1 | H | H | sNp1 | H |
| 315 | Ir | 3 | Py1 | Tn1 | H | H | sTn1 | H |
| 316 | Ir | 3 | Py1 | Tn1 | H | H | sTn3 | H |
| 317 | Ir | 3 | Py1 | Tn3 | H | H | sPh | H |
| 318 | Ir | 3 | Py1 | Tn3 | H | H | sNp1 | H |

TABLE 7-continued

| No | M | m | CyN1 | CyC1 | R1 | R2 | R3 | R4 |
|---|---|---|---|---|---|---|---|---|
| 319 | Ir | 3 | Py1 | Tn3 | H | H | sTn1 | H |
| 320 | Ir | 3 | Py1 | Tn3 | H | H | sTn3 | H |
| 321 | Ir | 3 | Py1 | Tn4 | H | H | sPh | H |
| 322 | Ir | 3 | Py1 | Tn4 | H | H | sNp1 | H |
| 323 | Ir | 3 | Py1 | Tn4 | H | H | sTn1 | H |
| 324 | Ir | 3 | Py1 | Tn4 | H | H | sTn3 | H |
| 325 | Ir | 3 | Py1 | Np2 | H | H | sPh | H |
| 326 | Ir | 3 | Py1 | Np2 | H | H | sNp1 | H |
| 327 | Ir | 3 | Py1 | Np2 | H | H | sTn1 | H |
| 328 | Ir | 3 | Py1 | Np2 | H | H | sTn3 | H |
| 329 | Ir | 3 | Py2 | Ph | H | H | sPh | H |
| 330 | Ir | 3 | Py2 | Ph | H | H | sNp1 | H |
| 331 | Ir | 3 | Py2 | Ph | H | H | sTn1 | H |
| 332 | Ir | 3 | Py2 | Ph | H | H | sTn3 | H |
| 333 | Ir | 3 | Py2 | Tn1 | H | H | sPh | H |
| 334 | Ir | 3 | Py2 | Tn1 | H | H | sNp1 | H |
| 335 | Ir | 3 | Py2 | Tn1 | H | H | sTn1 | H |
| 336 | Ir | 3 | Py2 | Tn1 | H | H | sTn3 | H |
| 337 | Ir | 3 | Py2 | Tn3 | H | H | sPh | H |
| 338 | Ir | 3 | Py2 | Tn3 | H | H | sNp1 | H |
| 339 | Ir | 3 | Py2 | Tn3 | H | H | sTn1 | H |
| 340 | Ir | 3 | Py2 | Tn3 | H | H | sTn3 | H |
| 341 | Ir | 3 | Py2 | Tn4 | H | H | sPh | H |
| 342 | Ir | 3 | Py2 | Tn4 | H | H | sNp1 | H |
| 343 | Ir | 3 | Py2 | Tn4 | H | H | sTn1 | H |
| 344 | Ir | 3 | Py2 | Tn4 | H | H | sTn3 | H |
| 345 | Ir | 3 | Py2 | Np2 | H | H | sPh | H |
| 346 | Ir | 3 | Py2 | Np2 | H | H | sNp1 | H |
| 347 | Ir | 3 | Py2 | Np2 | H | H | sTn1 | H |
| 348 | Ir | 3 | Py2 | Np2 | H | H | sTn3 | H |
| 349 | Ir | 3 | Pr | Ph | sPh | H | H | H |
| 350 | Ir | 3 | Pr | Ph | sNp2 | H | H | H |
| 351 | Ir | 3 | Pr | Ph | sTn1 | H | H | H |
| 352 | Ir | 3 | Pr | Ph | sTn3 | H | H | H |
| 353 | Ir | 3 | Pr | Tn1 | sPh | H | H | H |
| 354 | Ir | 3 | Pr | Tn1 | sNp2 | H | H | H |
| 355 | Ir | 3 | Pr | Tn1 | sTn1 | H | H | H |
| 356 | Ir | 3 | Pr | Tn1 | sTn3 | H | H | H |
| 357 | Ir | 3 | Pr | Tn3 | sPh | H | H | H |
| 358 | Ir | 3 | Pr | Tn3 | sNp2 | H | H | H |
| 359 | Ir | 3 | Pr | Tn3 | sTn1 | H | H | H |
| 360 | Ir | 3 | Pr | Tn3 | sTn3 | H | H | H |
| 361 | Ir | 3 | Pr | Np2 | sPh | H | H | H |
| 362 | Ir | 3 | Pr | Np2 | sNp2 | H | H | H |
| 363 | Ir | 3 | Pr | Np2 | sTn1 | H | H | H |
| 364 | Ir | 3 | Pr | Np2 | sTn3 | H | H | H |

TABLE 8

| No | M | m | CyN1 | CyC1 | R1 | R2 | R3 | R4 |
|---|---|---|---|---|---|---|---|---|
| 365 | Ir | 3 | Pz | Ph | sPh | H | H | H |
| 366 | Ir | 3 | Pz | Ph | sNp2 | H | H | H |
| 367 | Ir | 3 | Pz | Ph | sTn1 | H | H | H |
| 368 | Ir | 3 | Pz | Ph | sTn3 | H | H | H |
| 369 | Ir | 3 | Pz | Tn1 | sPh | H | H | H |
| 370 | Ir | 3 | Pz | Tn1 | sNp2 | H | H | H |
| 371 | Ir | 3 | Pz | Tn1 | sTn1 | H | H | H |
| 372 | Ir | 3 | Pz | Tn1 | sTn3 | H | H | H |
| 373 | Ir | 3 | Pz | Tn3 | sPh | H | H | H |
| 374 | Ir | 3 | Pz | Tn3 | sNp2 | H | H | H |
| 375 | Ir | 3 | Pz | Tn3 | sTn1 | H | H | H |
| 376 | Ir | 3 | Pz | Tn3 | sTn3 | H | H | H |
| 377 | Ir | 3 | Pz | Np2 | sPh | H | H | H |
| 378 | Ir | 3 | Pz | Np2 | sNp2 | H | H | H |
| 379 | Ir | 3 | Pz | Np2 | sTn1 | H | H | H |
| 380 | Ir | 3 | Pz | Np2 | sTn3 | H | H | H |

TABLE 9

| No | M | m | CyN1 | CyC1 | R1 | R2 | R3 | R4 | R5 | R6 |
|---|---|---|---|---|---|---|---|---|---|---|
| 381 | Ir | 3 | Pr | Ph | sPh | H | H | H | H | —NO2 |
| 382 | Ir | 3 | Pr | Ph | sNp2 | H | —CH3 | H | H | H |
| 383 | Ir | 3 | Pr | Ph | sTn1 | H | H | H | —CF3 | H |
| 384 | Ir | 3 | Pr | Ph | sTn3 | H | H | H | H | sPh |
| 385 | Ir | 3 | Pr | Tn1 | sPh | H | H | H | —OCH$_3$ | H |
| 386 | Ir | 3 | Pr | Tn1 | sNp2 | H | H | H | H | sPh |
| 387 | Ir | 3 | Pr | Tn1 | sTn1 | H | H | H | H | —CF3 |
| 388 | Ir | 3 | Pr | Tn1 | sTn3 | H | H | H | H | sPh |
| 389 | Ir | 3 | Pr | Tn3 | sPh | H | H | H | —OCH$_3$ | H |
| 390 | Ir | 3 | Pr | Tn3 | sNp2 | H | H | H | H | —OCH$_3$ |
| 391 | Ir | 3 | Pr | Tn3 | sTn1 | H | H | H | H | —OCH$_3$ |
| 392 | Ir | 3 | Pr | Tn3 | sTn3 | H | H | H | —OCH$_3$ | H |
| 393 | Ir | 3 | Pr | Np2 | sPh | H | H | H | —OCH$_3$ | H |
| 394 | Ir | 3 | Pr | Np2 | sNp2 | H | H | H | H | sPh |
| 395 | Ir | 3 | Pr | Np2 | sTn1 | H | H | H | H | sPh |
| 396 | Ir | 3 | Pr | Np2 | sTn3 | H | H | H | H | —OCH$_3$ |
| 397 | Ir | 3 | Pz | Ph | sPh | H | H | —OCH$_3$ | H | H |
| 398 | Ir | 3 | Pz | Ph | sNp2 | H | H | —OCH$_3$ | H | H |
| 399 | Ir | 3 | Pz | Ph | sTn1 | H | H | H | H | —OCH$_3$ |
| 400 | Ir | 3 | Pz | Ph | sTn3 | H | H | H | H | —OCH$_3$ |
| 401 | Ir | 3 | Pz | Tn1 | sPh | H | —C3H7 | H | H | H |
| 402 | Ir | 3 | Pz | Tn1 | sNp2 | H | H | H | H | H |
| 403 | Ir | 3 | Pz | Tn1 | sTn1 | H | H | H | H | H |
| 404 | Ir | 3 | Pz | Tn1 | sTn3 | H | H | H | H | sPh |
| 405 | Ir | 3 | Pz | Tn3 | sPh | H | H | H | H | —OCH$_3$ |
| 406 | Ir | 3 | Pz | Tn3 | sNp2 | H | H | —OCH$_3$ | H | H |
| 407 | Ir | 3 | Pz | Tn3 | sTn1 | H | H | —OCH$_3$ | H | H |
| 408 | Ir | 3 | Pz | Tn3 | sTn3 | H | H | H | H | —OCH$_3$ |
| 409 | Ir | 3 | Pz | Np2 | sPh | H | H | H | H | —OCH$_3$ |
| 410 | Ir | 3 | Pz | Np2 | sNp2 | H | —C3H7 | H | H | H |

TABLE 10

| No | M | m | CyN1 | CyC1 | R1 | R2 | R3 | R4 | R5 | R6 |
|---|---|---|---|---|---|---|---|---|---|---|
| 411 | Ir | 3 | Pz | Np2 | sTn1 | H | H | —CF3 | H | H |
| 412 | Ir | 3 | Pz | Np2 | sTn3 | H | H | —CF3 | H | H |
| 413 | Ir | 3 | Ta | Ph | C4H9 | C4H9 | sPh | H | OCH3 | H |
| 414 | Ir | 3 | Pr | Ph | sPh | H | H | H | H | H |
| 415 | Ir | 3 | Pr | Ph | sNp2 | H | —CH3 | H | H | H |
| 416 | Ir | 3 | Pr | Ph | sTn1 | H | H | H | H | H |
| 417 | Ir | 3 | Pr | Ph | sTn3 | H | H | H | H | H |
| 418 | Ir | 3 | Pr | Tn1 | sPh | H | H | H | —OCH$_3$ | H |
| 419 | Ir | 3 | Pr | Tn1 | sNp2 | H | H | H | H | H |
| 420 | Ir | 3 | Pr | Tn1 | sTn1 | H | H | H | H | H |
| 421 | Ir | 3 | Pr | Tn1 | sTn3 | H | H | H | H | H |
| 422 | Ir | 3 | Pr | Tn3 | sPh | H | H | H | —OCH$_3$ | H |
| 423 | Ir | 3 | Pr | Tn3 | sNp2 | H | H | H | H | H |
| 424 | Ir | 3 | Pr | Tn3 | sTn1 | H | —NO2 | H | H | H |
| 425 | Ir | 3 | Pr | Tn3 | sTn3 | H | H | H | H | H |
| 426 | Ir | 3 | Pr | Np2 | sPh | H | H | H | H | H |
| 427 | Ir | 3 | Pr | Np2 | sNp2 | H | H | H | H | H |
| 428 | Ir | 3 | Pr | Np2 | sTn1 | H | H | H | H | H |
| 429 | Ir | 3 | Pr | Np2 | sTn3 | H | H | H | H | H |
| 430 | Ir | 3 | Pz | Ph | sPh | H | H | —F | H | H |
| 431 | Ir | 3 | Pz | Ph | sNp2 | H | H | H | H | H |
| 432 | Ir | 3 | Pz | Ph | sTn1 | —CN | H | H | H | H |
| 433 | Ir | 3 | Pz | Ph | sTn3 | H | H | H | H | H |
| 434 | Ir | 3 | Pz | Tn1 | sPh | H | —C3H7 | H | H | H |
| 435 | Ir | 3 | Pz | Tn1 | sNp2 | H | H | —CH2—CH=CH—CH3 | H | H |

TABLE 10-continued

| No | M | m | CyN1 | CyC1 | R1 | R2 | R3 | R4 | R5 | R6 |
|---|---|---|---|---|---|---|---|---|---|---|
| 436 | Ir | 3 | Pz | Tn1 | sTn1 | H | H | H | H | H |
| 437 | Ir | 3 | Pz | Tn1 | sTn3 | H | H | H | H | H |
| 438 | Ir | 3 | Pz | Tn3 | sPh | H | —SC3H7 | H | H | H |
| 439 | Ir | 3 | Pz | Tn3 | sNp2 | H | H | H | H | H |
| 440 | Ir | 3 | Pz | Tn3 | sTn1 | H | H | H | H | H |
| 441 | Ir | 3 | Pz | Tn3 | sTn3 | H | H | H | H | H |
| 442 | Ir | 3 | Pz | Np2 | sPh | H | H | H | H | H |
| 443 | Ir | 3 | Pz | Np2 | sNp2 | H | H | H | H | H |
| 444 | Ir | 3 | Pz | Np2 | sTn1 | H | H | H | H | H |
| 445 | Ir | 3 | Pz | Np2 | sTn3 | H | H | H | H | H |

TABLE 11

| No | M | m | n | CyN1 | CyC1 | CyN2 | CyC2 | R1 | R2 | R3 | R4 | R1' | R2' | R3' | R4' |
|---|---|---|---|---|---|---|---|---|---|---|---|---|---|---|---|
| 446 | Ir | 2 | 1 | Pr | Ph | Pr | Tn1 | sPh | H | H | H | sPh | H | H | H |
| 447 | Ir | 2 | 1 | Pr | Ph | Pr | Tn1 | sNp2 | H | H | H | sNp2 | H | H | H |
| 448 | Ir | 2 | 1 | Pr | Ph | Pr | Tn1 | sTn1 | H | H | H | sTn1 | H | H | H |
| 449 | Ir | 2 | 1 | Pr | Ph | Pr | Tn1 | sTn3 | H | H | H | sTn3 | H | H | H |
| 450 | Ir | 2 | 1 | Pr | Tn3 | Pr | Np2 | sPh | H | H | H | sPh | H | H | H |
| 451 | Ir | 2 | 1 | Pr | Tn3 | Pr | Np2 | sNp2 | H | H | H | sNp2 | H | H | H |
| 452 | Ir | 2 | 1 | Pr | Tn3 | Pr | Np2 | sTn1 | H | H | H | sTn1 | H | H | H |
| 453 | Ir | 2 | 1 | Pr | Tn3 | Pr | Np2 | sTn3 | H | H | H | sTn3 | H | H | H |

TABLE 12

| No | M | m | n | CyN1 | CyC1 | E | G | R1 | R2 | R3 | R4 |
|---|---|---|---|---|---|---|---|---|---|---|---|
| 454 | Ir | Ir | 1 | Pr | Ph | —CH3 | —CH3 | sPh | H | H | H |
| 455 | Ir | Ir | 1 | Pr | Ph | —CH3 | —CH3 | sNp2 | H | H | H |
| 456 | Ir | Ir | 1 | Pr | Ph | —CH3 | —CH3 | sTn1 | H | H | H |
| 457 | Ir | Ir | 1 | Pr | Ph | —CH3 | —CH3 | H | H | sTn3 | H |
| 458 | Ir | Ir | 1 | Pr | Tn3 | —CH3 | sPh | H | H | sPh | H |
| 459 | Ir | Ir | 1 | Pr | Tn3 | —CH3 | sPh | H | H | sNp2 | H |
| 460 | Ir | Ir | 1 | Pr | Tn3 | —CH3 | sPh | H | H | sTn1 | H |
| 461 | Ir | Ir | 1 | Pr | Tn3 | —CH3 | sPh | H | H | sTn3 | H |

TABLE 13

| No | M | m | CyN1 | CyC1 | R1 | R2 | R3 | R4 |
|---|---|---|---|---|---|---|---|---|
| 462 | Rh | 3 | Pr | Ph | sPh | H | H | H |
| 463 | Rh | 3 | Pr | Ph | sNp2 | H | H | H |
| 464 | Rh | 3 | Pr | Ph | sTn1 | H | H | H |
| 465 | Rh | 3 | Pr | Ph | sTn3 | H | H | H |
| 466 | Rh | 3 | Pr | Tn1 | sPh | H | H | H |
| 467 | Rh | 3 | Pr | Tn1 | sNp2 | H | H | H |
| 468 | Rh | 3 | Pr | Tn1 | sTn1 | H | H | H |
| 469 | Rh | 3 | Pr | Tn1 | sTn3 | H | H | H |
| 470 | Rh | 3 | Pr | Tn3 | sPh | H | H | H |
| 471 | Rh | 3 | Pr | Tn3 | sNp2 | H | H | H |
| 472 | Rh | 3 | Pr | Tn3 | sTn1 | H | H | H |
| 473 | Rh | 3 | Pr | Tn3 | sTn3 | H | H | H |
| 474 | Rh | 3 | Pr | Np2 | sPh | H | H | H |
| 475 | Rh | 3 | Pr | Np2 | sNp2 | H | H | H |
| 476 | Rh | 3 | Pr | Np2 | sTn1 | H | H | H |
| 477 | Rh | 3 | Pr | Np2 | sTn3 | H | H | H |

TABLE 14

| No | M | m | CyN1 | CyC1 | R1 | R2 | R3 | R4 |
|---|---|---|---|---|---|---|---|---|
| 478 | Pt | 2 | Pr | Ph | sPh | H | H | H |
| 479 | Pt | 2 | Pr | Ph | sNp2 | H | H | H |
| 480 | Pt | 2 | Pr | Ph | sTn1 | H | H | H |
| 481 | Pt | 2 | Pr | Ph | sTn3 | H | H | H |
| 482 | Pt | 2 | Pr | Tn1 | sPh | H | H | H |
| 483 | Pt | 2 | Pr | Tn1 | sNp2 | H | H | H |
| 484 | Pt | 2 | Pr | Tn1 | sTn1 | H | H | H |
| 485 | Pt | 2 | Pr | Tn1 | sTn3 | H | H | H |
| 486 | Pt | 2 | Pr | Tn3 | sPh | H | H | H |
| 487 | Pt | 2 | Pr | Tn3 | sNp2 | H | H | H |
| 488 | Pt | 2 | Pr | Tn3 | sTn1 | H | H | H |
| 489 | Pt | 2 | Pr | Tn3 | sTn3 | H | H | H |
| 490 | Pt | 2 | Pr | Np2 | sPh | H | H | H |
| 491 | Pt | 2 | Pr | Np2 | sNp2 | H | H | H |
| 492 | Pt | 2 | Pr | Np2 | sTn1 | H | H | H |
| 493 | Pt | 2 | Pr | Np2 | sTn3 | H | H | H |

TABLE 15

| No | M | m | CyN1 | CyC1 | R1 | R2 | R3 | R4 |
|---|---|---|---|---|---|---|---|---|
| 494 | Pd | 2 | Pr | Ph | sPh | H | H | H |
| 495 | Pd | 2 | Pr | Ph | sNp2 | H | H | H |
| 496 | Pd | 2 | Pr | Ph | sTn1 | H | H | H |
| 497 | Pd | 2 | Pr | Ph | sTn3 | H | H | H |
| 498 | Pd | 2 | Pr | Tn1 | sPh | H | H | H |
| 499 | Pd | 2 | Pr | Tn1 | sNp2 | H | H | H |
| 500 | Pd | 2 | Pr | Tn1 | sTn1 | H | H | H |
| 501 | Pd | 2 | Pr | Tn1 | sTn3 | H | H | H |
| 502 | Pd | 2 | Pr | Tn3 | sPh | H | H | H |
| 503 | Pd | 2 | Pr | Tn3 | sNp2 | H | H | H |
| 504 | Pd | 2 | Pr | Tn3 | sTn1 | H | H | H |
| 505 | Pd | 2 | Pr | Tn3 | sTn3 | H | H | H |
| 506 | Pd | 2 | Pr | Np2 | sPh | H | H | H |

TABLE 15-continued

| No | M | m | CyN1 | CyC1 | R1 | R2 | R3 | R4 |
|---|---|---|---|---|---|---|---|---|
| 507 | Pd | 2 | Pr | Np2 | sNp2 | H | H | H |
| 508 | Pd | 2 | Pr | Np2 | sTn1 | H | H | H |
| 509 | Pd | 2 | Pr | Np2 | sTn3 | H | H | H |

TABLE 16

| No | M | m | CyN1 | CyC1 | R1 | R2 | R3 | R4 | R5 | R6 |
|---|---|---|---|---|---|---|---|---|---|---|
| 510 | Ir | 3 | Pr | Ph | sPe | H | H | H | H | H |
| 511 | Ir | 3 | Pr | Ph | sPh | H | sPh | H | 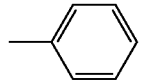 | H |
| 512 | Ir | 3 | Pr | Ph | H | 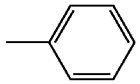 | sPh | H | H | 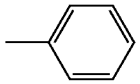 |
| 513 | Ir | 3 | Pr | Np2 | sPe | H | H | H | H | H |
| 514 | Ir | 3 | Pr | Np2 | H | H | sTn1 | H | CH3 | H |
| 515 | Ir | 3 | Pr | Tn1 | CH3 | H | sTn1 | H | CH3 | H |
| 516 | Ir | 3 | Pr | Tn1 | sPh | H | sTn1 | H | sPh | H |

TABLE 17

| No | M | m | n | CyN1 | CyC1 | R1 | R2 | R3 | R4 | E | G |
|---|---|---|---|---|---|---|---|---|---|---|---|
| 517 | Ir | 2 | 1 | Pr | Tn3 | H | H | sPh | H | CH3 | CH3 |
| 518 | Ir | 2 | 1 | Pr | Tn1 | H | H | sTn1 | H | CH3 | CH3 |
| 519 | Ir | 2 | 1 | Pr | Np2 | H | H | sNp2 | H | CH3 | CH3 |
| 520 | Ir | 3 | 0 | Py1 | Ph | sPh | H | H | H | — | — |
| 521 | Ir | 3 | 0 | Py1 | Ph | sNp1 | H | H | H | — | — |
| 522 | Ir | 3 | 0 | Pr | Ph | H | H | H | sPh | — | — |
| 523 | Ir | 3 | 0 | Pr | Ph | H | sPh | H | H | — | — |
| 524 | Ir | 3 | 0 | Pr | Tn1 | Ph | H | H | H | — | — |
| 525 | Ir | 2 | 1 | Py1 | Ph | sPh | H | H | H | CH3 | CH3 |
| 526 | Ir | 2 | 1 | Py1 | Ph | sNp1 | H | H | H | CH3 | CH3 |
| 527 | Ir | 2 | 1 | Pr | Ph | H | H | H | sPh | CH3 | CH3 |
| 528 | Ir | 2 | 1 | Pr | Ph | H | sPh | H | H | CH3 | CH3 |
| 529 | Ir | 2 | 1 | Pr | Tn1 | Ph | H | H | H | CH3 | CH3 |

Hereinbelow, the present invention will be described more specifically based on Examples.

EXAMPLES 1–6

Each of luminescence devices having a layer structure shown in FIG. 1B were prepared in the following manner.

On a 1.1 mm-thick glass substrate (transparent substrate 15), a 100 nm-thick film (transparent electrode 14) of ITO (indium tin oxide) was formed by sputtering, followed by patterning to form a stripe electrode including 100 lines each having a width of 100 nm and a spacing with an adjacent line of 10 nm (i.e., electrode pitch of 110 nm).

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (30 nm): co-deposited film of CBP:metal complex (metal coordination compound shown in Table 20) (95:5 by weight)

Organic layer 3 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

The above-deposited metal electrode layers 1 and 2 (Al—Li layer and Al layer) had a stripe electrode pattern including 100 lines each having a width of 100 nm and a spacing of 10 nm (electrode pitch=110 nm) and arranged so that the stripe electrode pattern intersected with that of the ITO electrode at right angles to form a matrix of pixels each having an effective electrode area of 3 mm² comprising 20 ITO lines bundled together at a lead-out portion and 15 Al (Al—Li) lines bundled together at a lead-out portion.

Each of the thus-prepared luminescence devices was taken out of the vacuum chamber and was subjected to a continuous energization (current passage) test in an atmosphere of dry nitrogen gas stream so as to remove device deterioration factors, such as oxygen and moisture (water content).

The continuous energization test was performed by continuously applying a voltage at a constant current density of 50 mA/cm² to the luminescence device having the ITO (transparent) electrode (as an anode) and the Al (metal) electrode (as a cathode), followed by measurement of emission luminance (brightness) with time so as to determine a time (luminance half-life) required for decreasing an initial luminance (60–220 cd/m²) to ½ thereof.

The results are shown in Table 18 appearing hereinafter.

COMPARATIVE EXAMPLE 1

A comparative luminescence device was prepared and evaluated in the same manner as in Examples 1–6 except that the Ir complexes (metal coordination compounds shown in Table 20) was changed to Ir-phenylpyridine complex (Ir(ppy)₃) shown below.

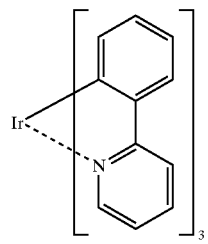

The results are also shown in Table 18 below.

TABLE 18

| Ex. No. | Compound No. | Luminance half-life (Hr) |
|---|---|---|
| Ex. 1 | 3 | 450 |
| Ex. 2 | 11 | 550 |
| Ex. 3 | 22 | 500 |
| Ex. 4 | 43 | 500 |
| Ex. 5 | 45 | 600 |
| Ex. 6 | 385 | 400 |
| Ex. 7 | 413 | 650 |
| Comp.Ex. 1 | Ir(ppy)₃ | 300 |

As is apparent from Table 18, compared with the conventional luminescence device using Ir(ppy)₃, the luminescence devices using the metal coordination compounds of formula (1) according to the present invention provide longer luminance half-lives, thus resulting in an EL device having a high durability (luminance stability) based on a good stability of the metal coordination compound of formula (1) of the present invention.

EXAMPLE 7

A color organic EL display apparatus shown in FIG. 2 was prepared in the following manner.

An active matrix substrate had a planar structure basically similar to a structure described in U.S. Pat. No. 6,114,715.

Specifically, on a 1.1 mm-thick glass substrate, top state-type TFTs of polycrystalline silicon were formed in an ordinary manner and thereon, a flattening film was formed with contact holes for electrical connection with a pixel electrode (anode) at respective source regions, thus preparing an active matrix substrate with a TFT circuit.

On the active matrix substrate, a 700 nm-thick pixel electrode (anode) of ITO having a larger work function was formed in a prescribed pattern. On the ITO electrode, prescribed organic layers and a 100 nm-thick Al electrode (cathode) were successively formed by vacuum deposition with a hard mask, followed by patterning to form a matrix of color pixels (128×128 pixels).

The respective organic layers corresponding to three color pixels (red (R) green (G) and blue (B)) were consisting of the following layers.

<R Pixel Region>
α-NPD (40 nm)/CBP: Ex. Comp. No. 22 (93:7 by weight) (30 nm)/BCP (20 nm)/Alq 3 (40 nm)
<G Pixel Region>
α-NPD (50 nm)/Alq 3 (50 nm)
<B Pixel Region>
α-NPD (50 nm)/BCP (20 nm)/Alq 3 (50 nm)

When the thus-prepared color organic EL display apparatus was driven, desired color image data can be displayed stably with good image qualities.

EXAMPLE 8

Synthesis of Example Compound No. 22

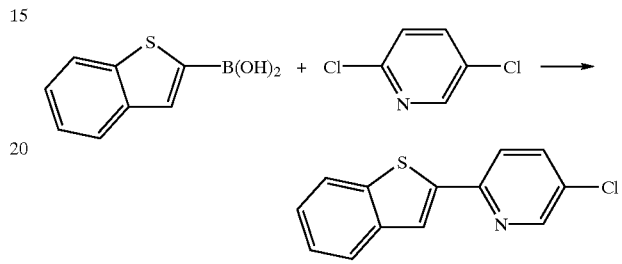

In a 500 ml-three-necked flask, 12.6 g (85.2 mM) of 2,5-dichloropyridine, 15.2 g (85.4 mM) of benzothiophene-2-boronic acid, 75 ml of toluene, 37.5 ml of ethanol and 75 ml of 2M-sodium carbonate aqueous solution were placed and stirred at room temperature under nitrogen stream, and 3.06 g (2.64 mM) of tetrakis(triphenylphosphine)palladium (0) was added thereto, followed by refluxing under stirring for 8 hours under nitrogen stream. After the reaction, the reaction mixture was cooled on an ice bath to precipitate a crystal, which was then filtered out and washed with water. To the crystal, 100 ml of methanol was added and washed under stirring at room temperature, followed by filtration to recover the crystal. The crystal was purified by silica gel column chromatography (eluent: chloroform) and recrystallized from a mixture solvent of chloroform-methanol to obtain 11.8 g (Yield: 56.4%) of 5-chloro-2-(benzo[b]thienyl) pyridine (colorless crystal).

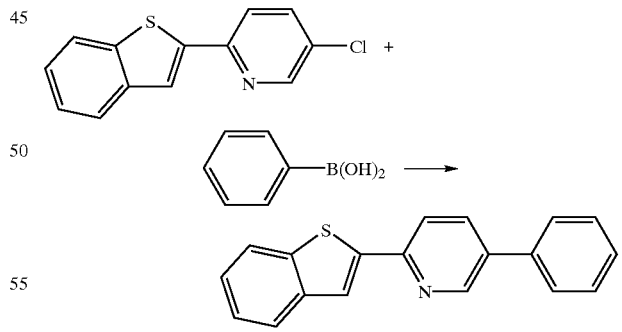

In a 100 ml-three-necked flask, 4.91 g (20.0 mM) of 5-chloro-2-(benzo[b]thienyl)pyridine, 3.66 g (30.0 mM) of phenylboronic acid, 9.58 g (40.0 mM) of tripotassium phosphate hydrate, 3.2 mg (0.020 mM) of palladium (II) acetate, 11.9 mg (0.040 mM) of 2-ditert-butylphosphinobiphenyl and 60 ml of toluene were placed and refluxed under stirring for 24 hours at 100° C. under nitrogen stream. After the reaction, the reaction mixture was cooled on an ice bath to precipitate a crystal, which was then filtered out and washed with water. To the crystal, 25 ml of methanol was added and washed under stirring at room temperature, followed by recovery by filtration. The crystal was purified by silica gel column chromatography (eluent: chloroform) and recrystallized from a chloroform-methanol mixture solvent to obtain 1.17 g (Yield: 20.4%) of 2-(benzo[b]thienyl)-5-phenylpyridine (colorless crystal).

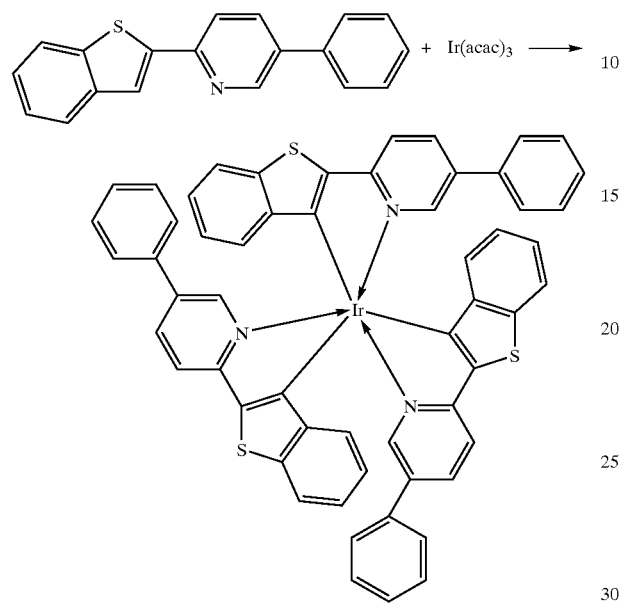

In a 100 ml-four-necked flask, 50 ml of glycerol was placed and heated at 130–140° C. under stirring and bubbling with nitrogen for 2 hours. Then, the glycerol was cooled by standing to 100° C., and 1.15 g (4.00 mM) of 2-(benzo[b]thienyl)-5-phenylpyridine and 0.40 g (0.82 mM) of iridium (III) acetylacetonate were added thereto, followed by stirring for 5 hours at 180–235° C. under nitrogen stream. The reaction mixture was cooled to room temperature and poured into 300 ml of 1N-hydrochloric acid to form a precipitate. The precipitate was recovered by filtration and washed with water, followed by drying for 5 hours at 100° C. under reduced pressure. The resultant precipitate was silica gel column chromatography (eluent: chloroform) to obtain 0.26 g (Yield: 30.2%) of red powdery tris[2-(benzo[b]thienyl)-5-phenylpyridine-$C^2$,N]iridium (III).

According to MALDI-TOF MS (matrix-assisted laser desorption ionization-time of flight mass spectroscopy), the compound exhibited M$^+$ (mass number of the corresponding cation formed by removal of 1 electron) of 1051.2, thus confirming the objective iridium complex.

When the compound was dissolved in toluene and subjected to measurement of phosphorescence spectrum at an excited light wavelength of 380 nm by using a fluorescence spectrometer, the compound exhibited a phosphorescence spectrum showing λmax (maximum emission wavelength) of 620 nm, thus confirming clear red luminescence.

When the luminescence device prepared in Example 3 using the above-synthesized metal coordination compound (Ex. Comp. No. 22) was subjected to measurement of phosphorescence spectrum in a similar manner, a clear red luminescence was confirmed similarly as in the case of the compound in toluene described above.

EXAMPLE 9

Synthesis of Ex. Comp. No. 11

A metal coordination compound (Ex. Comp. No. 11) was synthesized through the following reaction schemes.

Hereinafter, the synthesis yield is simply represented by "Y".

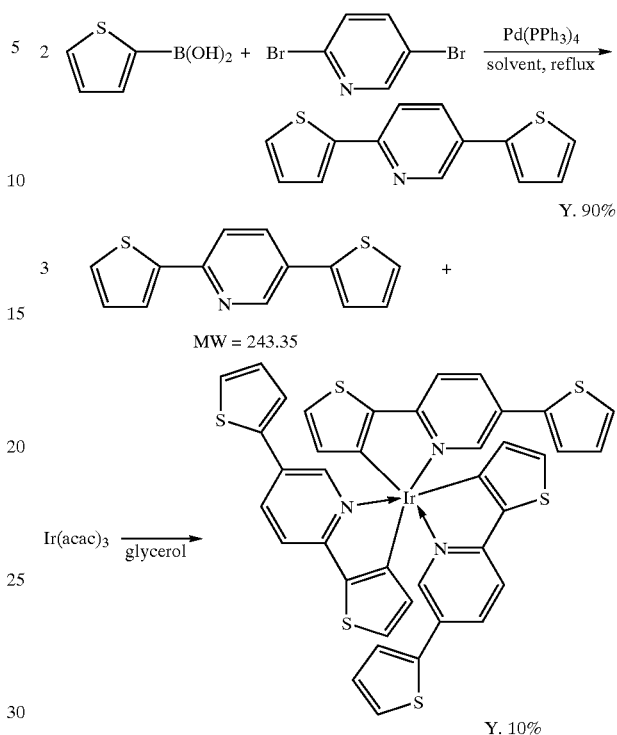

According to MALDI-TOF MS, the compound exhibited M$^+$=919.0, thus being identified as the objective iridium compound.

When the compound was dissolved in toluene and subjected to measurement of phosphorescence spectrum at an excited light wavelength of 400 nm by using a fluorescence spectrometer, the compound exhibited a phosphorescence spectrum showing λmax (maximum emission wavelength) of 612 nm, thus confirming clear red luminescence.

When a luminescence device having a layer structure shown below and using the above-synthesized metal coordination compound (Ex. Comp. No. 11) was prepared and subjected to measurement of phosphorescence spectrum in a similar manner, a clear red luminescence was confirmed similarly as in the case of the compound in toluene described above.

ITO (100 nm)/α-NPD (40 nm)/CBP: Ex. Comp. No. 11 (95:5 by weight)(30 nm)/BCP (20 nm)/Alq3 (40 nm)/Al—Li (1 nm)/Al (100 nm).

Further, the luminescence device exhibited a good rectifying characteristic.

Figure 3A:
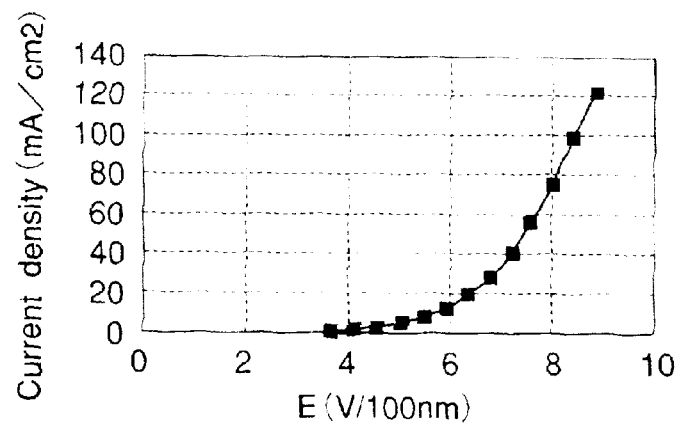
Figure 3B:
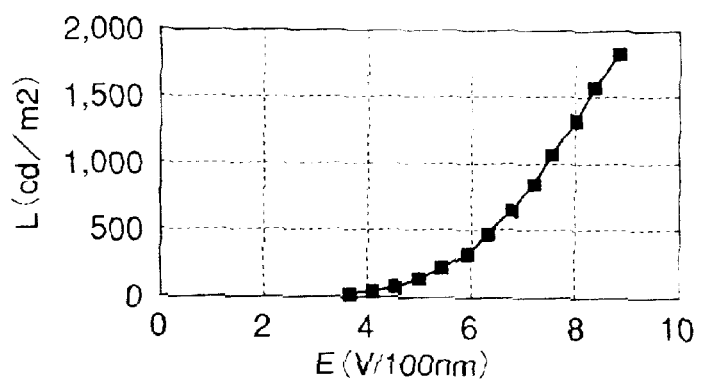
Figure 3C:
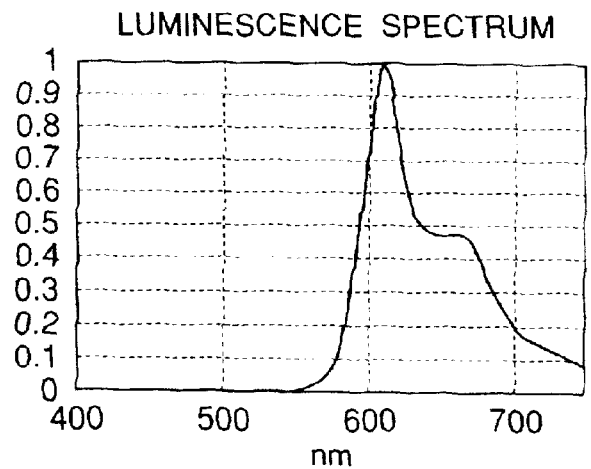

Specifically, FIG. 3A is a graph showing a relationship between an electric field strength (E) and a current density of the luminescence device, and FIG. 3B is a graph showing a relationship between an electric field strength (E) and a luminance (L) of the luminescence device. Further, FIG. 3C shows a luminescence spectrum of the luminescence device under application of a voltage of 10 volts.

The luminescence device exhibited a luminescence efficiency of 0.8 lm/W under application of a voltage of 10 volts. The luminescence device also emitted stable luminescence even when the luminescence device was continuously supplied with the voltage for ca. 200 hours.

EXAMPLE 10

Synthesis of Ex. Comp. No. 45

A metal coordination compound (Ex. Comp. No. 45) was synthesized through the following reaction schemes.

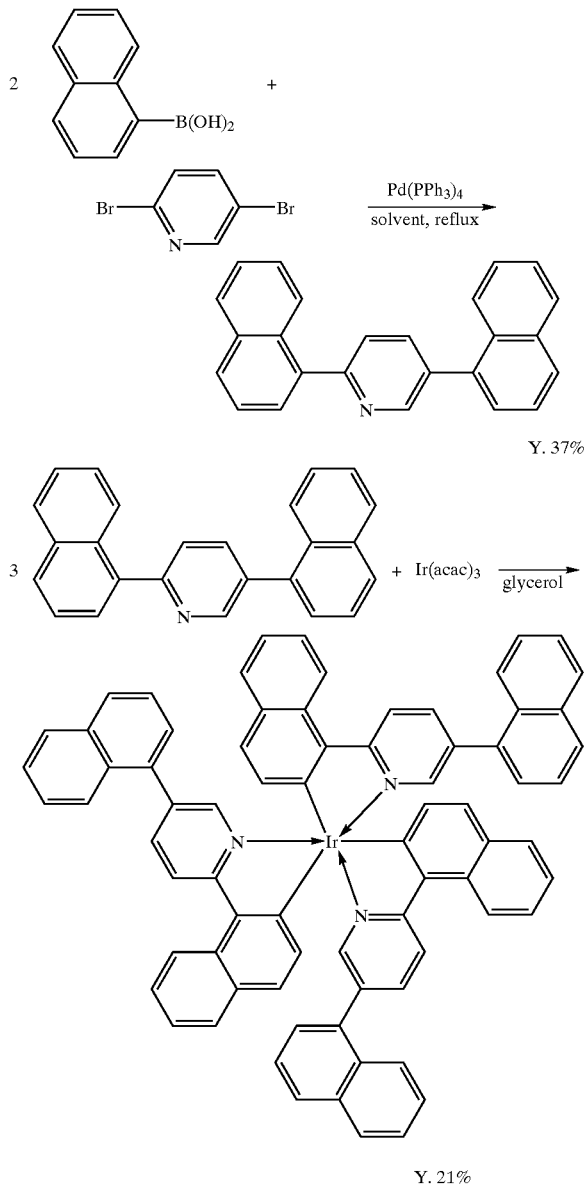

Y. 37%

Y. 21%

According to MALDI-TOF MS, the compound exhibited M+=1183.3, thus being identified as the objective iridium compound.

When the compound was dissolved in toluene and subjected to measurement of phosphorescence spectrum at an excited light wavelength of 380 nm by using a fluorescence spectrometer, the compound exhibited a phosphorescence spectrum showing λmax (maximum emission wavelength) of 603 nm, thus confirming clear reddish orange luminescence.

When the luminescence device prepared in Example 5 using the above-synthesized metal coordination compound (Ex. Comp. No. 45) was subjected to measurement of phosphorescence spectrum in a similar manner, a clear reddish orange luminescence was confirmed similarly as in the case of the compound in toluene described above.

Further, the luminescence device exhibited a good rectifying characteristic.

The luminescence device exhibited a luminescence efficiency of 0.5 lm/W under application of a voltage of 8 volts. The luminescence device also emitted stable luminescence even when the luminescence device was continuously supplied with the voltage for ca. 150 hours.

EXAMPLE 11

Another Synthesis of Ex. Comp. No. 22

Tris[2-(benzo[b]thienyl)-5-phenylpyridine-$C^2$,N]iridium (III) (Ex. Comp. No. 22) prepared in Example 8 was synthesized through another reaction schemes shown below.

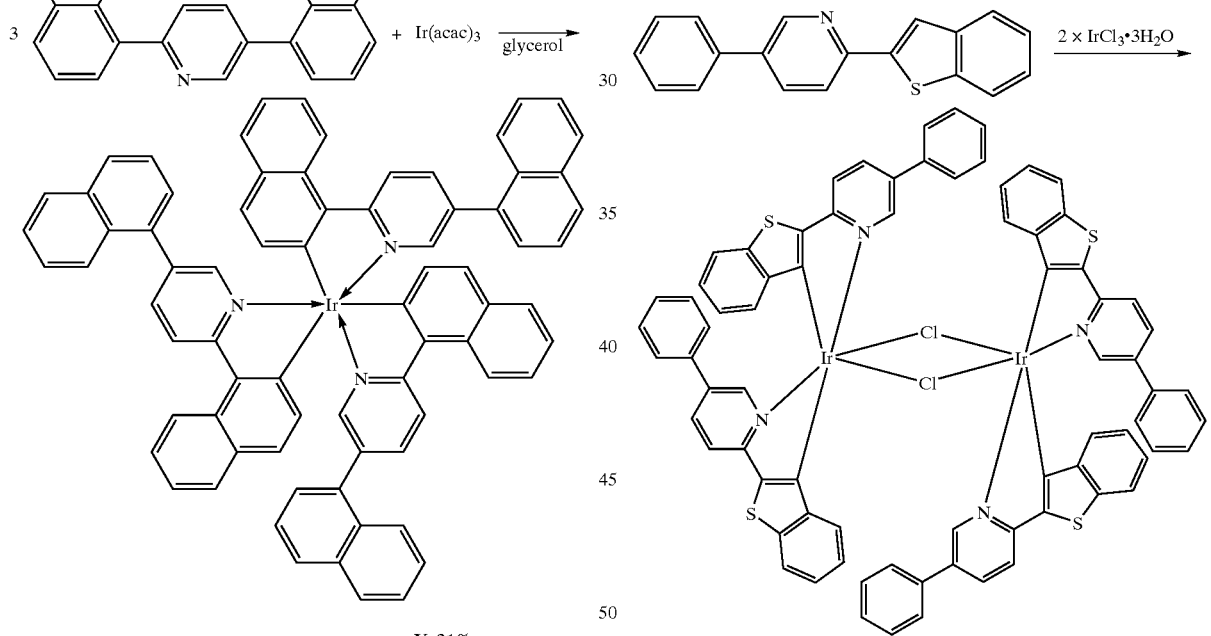

In a 200 ml-three-necked flask, 0.58 mg (1.64 mmole) of iridium (III) chloride-trihydrate (made by Across Organics Co.), 1.5 g (5.22 mmole) of 2-(benzo[b]thienyl)-5-phenylpyridine, 45 ml of ethoxyethanol and 15 ml of water were placed and stirred for 30 min. at room temperature under nitrogen stream, followed by 24 hours of reflux under stirring. The reaction product was cooled to room temperature, and the precipitate was recovered by filtration and washed with water, followed successive washing with ethanol and acetone. After drying under a reduced pressure at room temperature, 1.02 g of red powdery tetrakis[2-(benzo[b]thienyl)-5-phenylpyridine-$C^2$,N]-($\mu$-dichloro) diiridium (III) was obtained.

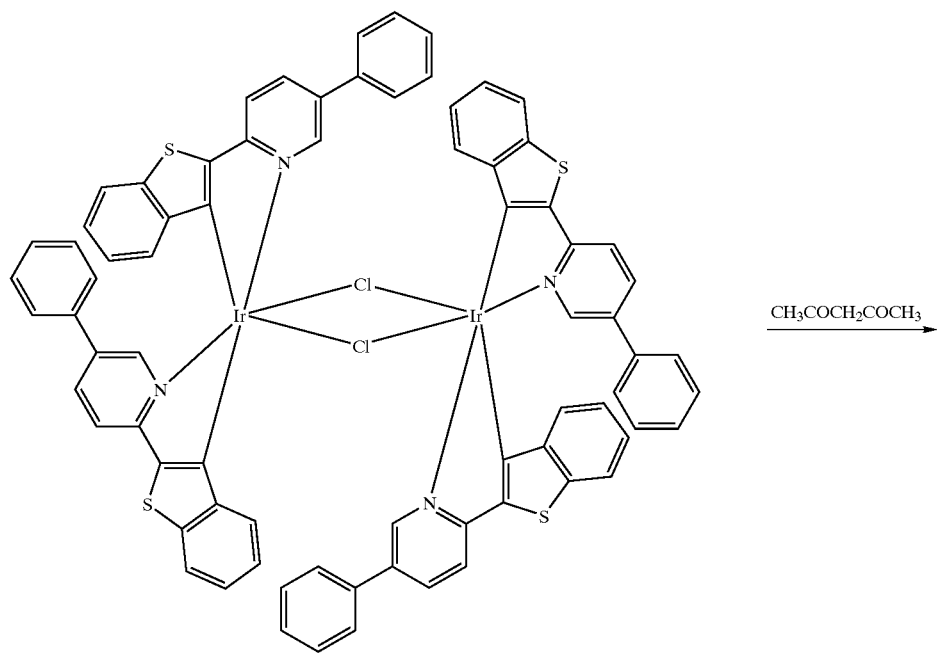

CH₃COCH₂COCH₃ →

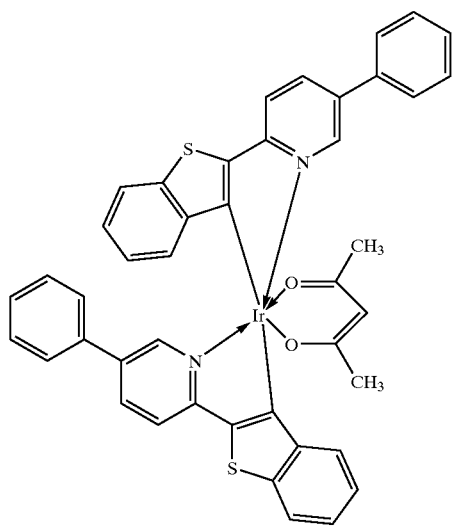

In a 200 ml-three-necked flask, 70 ml of ethoxyethanol, 0.95 g (0.72 mmole) of tetrakis[2-(benzo[b]thienyl)-5-phenylpyridine-$C^2$ N]($\mu$-dichloro)-diiridium (III), 0.22 g (2.10 mM) of acetylacetone and 1.04 g (9.91 mM) of sodium carbonate, were placed and stirred for 1 hour at room temperature under nitrogen stream and then refluxed under stirring for 15 hours. The reaction product was cooled with ice, and the precipitate was filtered out and washed with water. The precipitate was then purified by silica gel column chromatography (eluent: chloroform/methanol=30/1) to obtain 0.43 g of red powdery bis[2-(benzo[b]thienyl)-5-phenylpyridine-$C^2$,N](acetylacetonato)-iridium (III) (Example Compound No. 517). According to MALDI-TOF MS, M⁺ of 864.2 of the compound was confirmed. A toluene solution of the compound exhibited a luminescence spectrum showing $\lambda$max=631 nm and a quantum yield of 0.18 relative to 1.0 of Ir(ppy)₃.

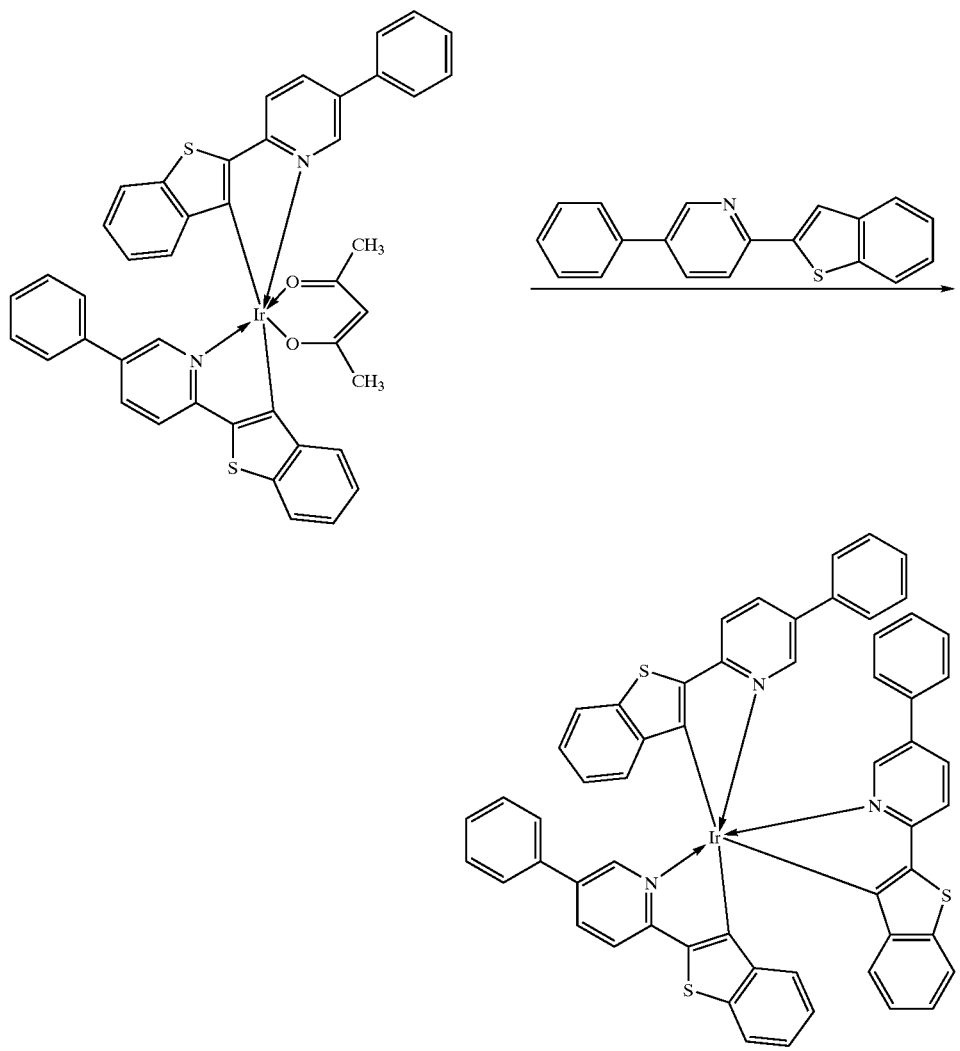

In a 100 ml-three-necked flask, 0.27 g (0.94 mM) of 2-(benzo[b]thienyl)-5-phenylpyridine, 0.36 g (0.42 mM) of bis[2-benzo[b]thienyl)-5-phenylpyridine-C², N] (acetylacetonato)iridium (III) and 25 ml of glycerol, were placed and heated around 180° C. for 8 hours under stirring and nitrogen stream. The reaction product was cooled to room temperature and poured into 170 ml of 1N-hydrochloric acid, and the precipitate was filtered out, washed with water and dried at 100° C. under a reduced pressure for 5 hours. The precipitate was purified by silica gel column chromatography with chloroform as the eluent to obtain 0.27 g of red powdery tris[2-(benzo[g]thienyl-5-phenylpyridine-C²,N]iridium (III) (Example Compound No. 22). According to MALDI-TOF MS, M⁺ of 1051.2 of the compound was confirmed. A toluene solution of the compound exhibited a luminescence spectrum showing λmax= 627 nm and a quantum yield of 0.17 relative to 1.0 of Ir(ppy)₃.

The above-synthesized compound and a luminescence device prepared by using the compound exhibited luminescence characteristics similar to those of the compound and luminescence device prepared in Example 8.

Bis[2-(benzo[g]thienyl)-5-phenylpyridine-C²,N]iridium (III) (Ex. Comp. No. 517) prepared in this example as an intermediate product exhibited λmax which was longer by ca. 4 nm than that of the final product (Ex. Comp. No. 22) having three identical ligands. Further, when a luminescence device using the intermediate product was prepared and evaluated in the same manner as in Example 8, the luminescence device exhibited a luminescence spectrum showing λmax=631 nm. Accordingly, the intermediate product used in this example can also be used as a luminescence material.

EXAMPLE 12

Another Synthesis of Ex. Comp. No. 45

The metal coordination compound (Ex. Comp. No. 45) prepared in Example 10 was synthesized through another reaction schemes shown below.

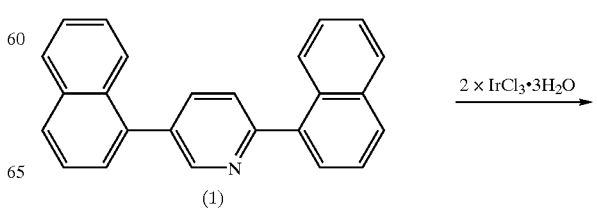

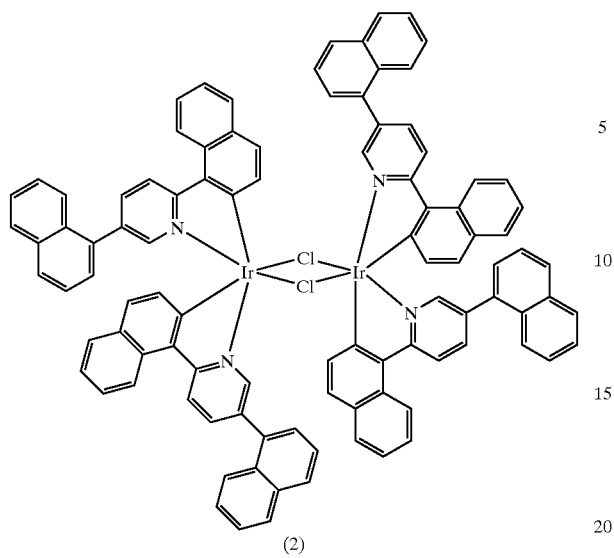

(2)

In a 200 ml-three-necked flask, 0.58 mg (1.64 mmole) of iridium (III) chloride-trihydrate (made by Across Organics Co.), 1.7 g (5.1 mmole) of a compound (1), 45 ml of ethoxyethanol and 15 ml of water were placed and stirred for 30 min. at room temperature under nitrogen stream, followed by 24 hours of reflux under stirring. The reaction product was cooled to room temperature, and the precipitate was recovered by filtration and washed with water, followed successive washing with ethanol and acetone. After drying under a reduced pressure at room temperature, 1.0 g (yield=93.4%) of red powdery compound (2) was obtained.

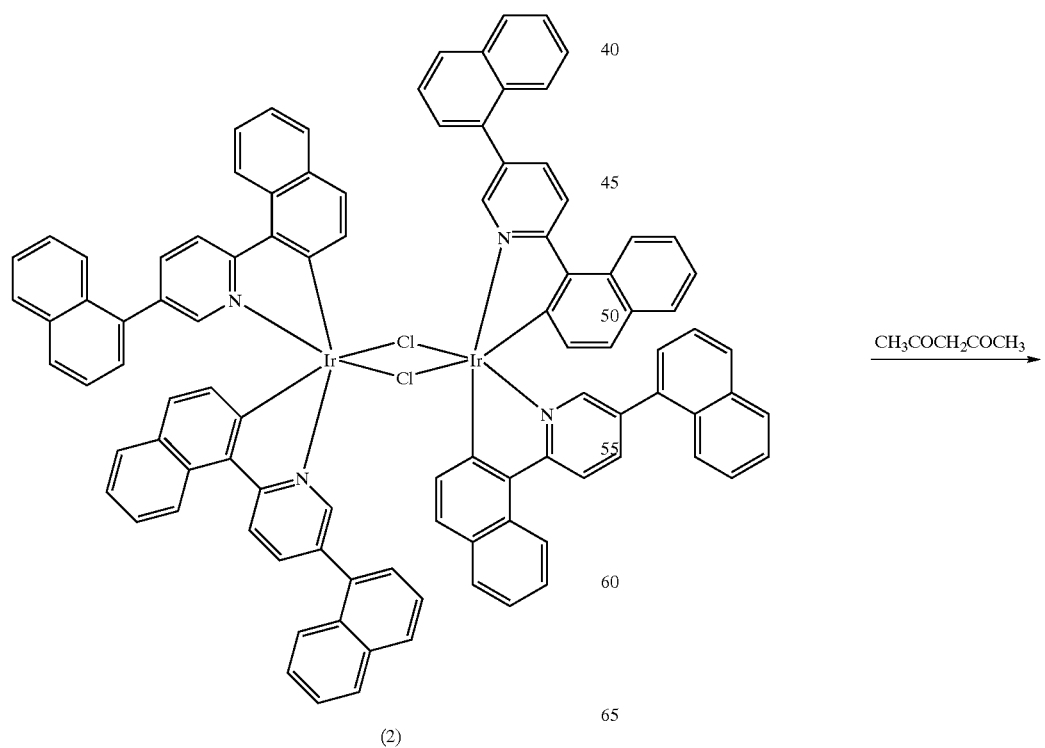

(2)

$$\xrightarrow{CH_3COCH_2COCH_3}$$

-continued

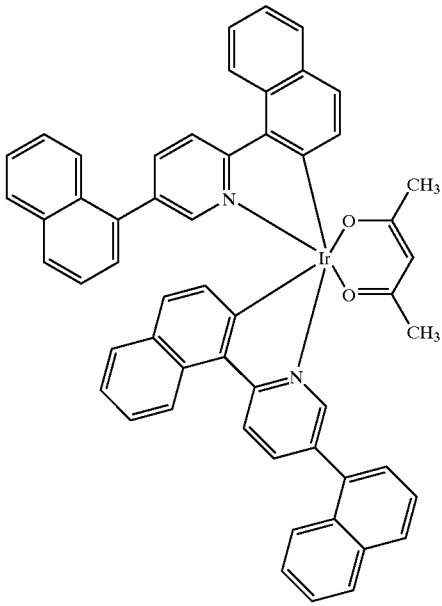

(3)

In a 200 ml-three-necked flask, 70 ml of ethoxyethanol, 0.90 g (0.71 mmole) of the compound (2), 0.22 g (2.10 mmole) of acetylacetone and 1.04 g (9.91 mmole) of sodium carbonate, were placed and stirred for 1 hour at room temperature under nitrogen stream and then refluxed under stirring for 15 hours. The reaction product was cooled with ice, and the precipitate was filtered out and washed with water. The precipitate was then purified by silica gel column chromatography (eluent: chloroform/methanol=30/1) to obtain 0.39 g of red powdery compound (3) (Example Compound No. 519). According to MALDI-TOF MS, M$^+$ of 952.3 of the compound was confirmed. A toluene solution of the compound exhibited a luminescence spectrum showing λmax=608 nm and a higher quantum yield of 0.30 relative to 1.0 of Ir(ppy)$_3$ in this emission wavelength region.

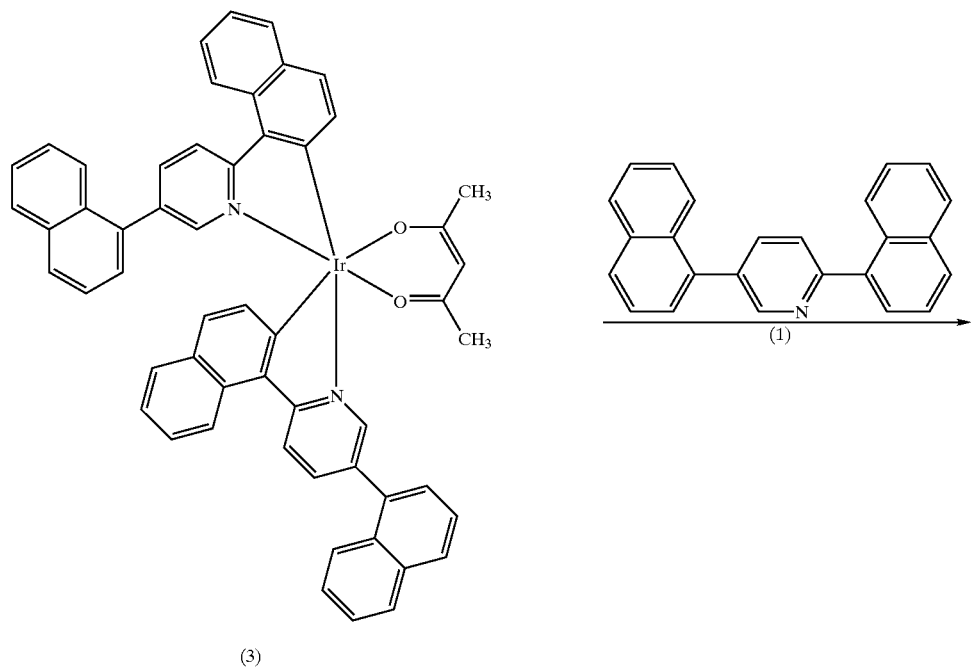

(3)                                                              (1)

-continued

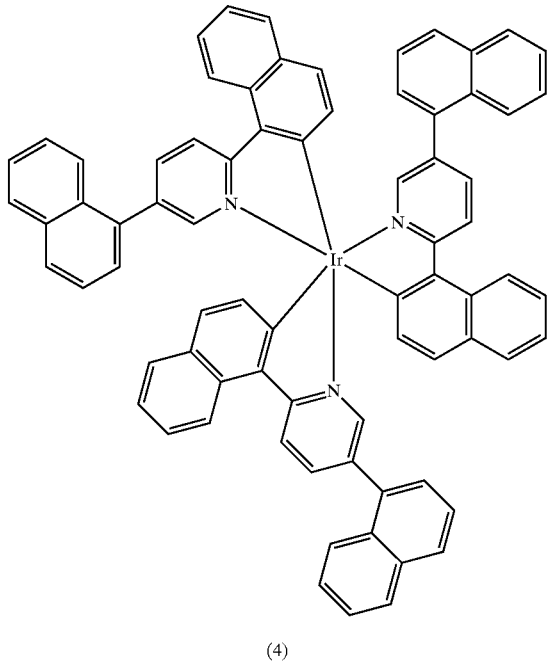

(4)

In a 100 ml-three-necked flask, 0.29 g (0.88 mM) of the compound (1) 0.34 g (0.35 mM) of the compound (3) and 25 ml of glycerol, were placed and heated around 180° C. for 8 hours under stirring and nitrogen stream. The reaction product was cooled to room temperature and poured into 170 ml of 1N-hydrochloric acid, and the precipitate was filtered out, washed with water and dried at 100° C. under a reduced pressure for 5 hours. The precipitate was purified by silica gel column chromatography with chloroform as the eluent to obtain 0.23 g of red powdery compound (4) (Example Compound No. 45). According to MALDI-TOF MS, $M^+$ of 1183.4 of the compound was confirmed. A toluene solution of the compound exhibited a luminescence spectrum showing λmax=603 nm and a quantum yield of 0.278 relative to 1.0 of Ir(ppy)$_3$.

The above-synthesized compound and a luminescence device prepared by using the compound exhibited luminescence characteristics similar to those of the compound and luminescence device prepared in Example 10.

The compound (3) (Ex. Comp. No. 519) prepared in this example as an intermediate product exhibited λmax which was longer by ca. 4 nm than that of the final product (Ex. Comp. No. 45) having three identical ligands. Further, when a luminescence device using the intermediate product was prepared and evaluated in the same manner as in Example 10, the luminescence device exhibited a luminescence spectrum showing λmax=608 nm and an external luminescence yield of 0.7 lm/W. Further, the luminescence device emitted stable luminescence even when continuously supplied with the voltage for ca. 100 hours. Accordingly, the intermediate product used in this example can also be used as a luminescence material.

EXAMPLE 13

Synthesis of Ex. Comp. Nos. 520 and 525

It is easy to synthesize the following compounds in the same manner as in Example 11 except that 4-chloropyrimidine is synthesized from 4(3H)-pyrimidone (made by Aldrich Co.) in the same manner as the process described at pages 37 and 38 of JP-A (Tokuhyo) 2001-504113 (corr. to U.S. Pat. No. 6,300,330) and is reacted with 4-phenylboronic acid (made by Lancaster Co.) to obtain 4-(biphenyl-4-yl)pyrimidine, which is used instead of 2-(benzo[b]thienyl)-5-phenylpyridine.

Bis[4-(biphenyl-4-yl)pyridine-$C^3,N^3$] (acetylacetonato) iridium (III) (Ex. Comp. No. 520).

Tris[4-(biphenyl-4-yl)pyrimidine-$C^3,N^3$] iridium (III) (Ex. Comp. No. 525).

EXAMPLE 14

Synthesis of Ex. Comp. Nos. 521 and 526

It is easy to synthesize the following compounds in the same manner as in Example 11 except that 4-(4-chlorophenyl)pyrimidine is synthesized from 4-chloropyrimidine prepared in Example 13 and 4-chlorophenylboronic acid (made by Aldrich Co.) and was reacted with 2-naphthaleneboronic acid (made by Lancaster Co.) to obtain 4-[4-(2-naphthyl)phenyl]-pyrimidine, which is used instead of 2-(benzo[b]thienyl)-5-phenylpyridine.

Bis{4-[4-(2-naphthyl)phenyl]pyrimidine-$C^3$, $N^3$} (acetylacetonato)iridium (III) (Ex. Comp. No. 521).

Tris{4-[4-(2-naphthyl)phenyl]pyrimidine-$C^3,N^3$}iridium (III) (Ex. Comp. No. 526).

EXAMPLE 15

Synthesis of Ex. Comp. Nos. 522 and 527

It is easy to synthesize the following compounds in the same manner as in Example 11 except that 2,4-diphenylpyridine is synthesized from phenylboronic acid (made by Tokyo Kasei Kogyo K.K.) and 4-phenyl-2-bromopyridine (made by General Intermediates of Canada) and was used instead of 2-(benzo[b]thienyl)-5-phenylpyridine.

Bis(2,4-diphenylpyridine-C², N¹)(acetylacetonato)iridium (III) (Ex. Comp. No. 522).

Tris(2,4-diphenylpyridine-C², N¹)iridium (III) (Ex. Comp. No. 527).

EXAMPLE 16

Synthesis of Ex. Comp. Nos. 523 and 528

It is easy to synthesize the following compounds in the same manner as in Example 11 except that 2-(biphenyl-3-yl)pyridine is synthesized from 3-biphenylboronic acid (made by Lancaster Co.) and 2-bromopyridine (made by Tokyo Kasei Kogyo K.K.) and is used instead of 2-(benzo [b]thienyl)-5-phenylpyridine.

Bis[2-(biphenyl-3-yl)pyridine-C⁴, N³)(acetylacetonato) iridium (III) (Ex. Comp. No. 523).

Tris[2-(biphenyl-2-yl)pyridine-C⁴, N³)iridium (III) (Ex. Comp. No. 528).

EXAMPLE 17

Synthesis of Ex. Comp. Nos. 524 and 529

It is easy to synthesize the following compounds in the same manner as in Example 11 except that 2-(5-bromothiophene-2-yl)pyridine is synthesized from 2-bromopyridine (made by Tokyo Kasei Kogyo K.K.) and 5-bromothiophene-2-boronic acid (made by Aldrich Co.) and was reacted with phenylboronic acid (made by Tokyo Kasei Kogyo K.K.) to obtain 2-(5-phenylthiophene-2-yl) pyridine, which is used instead of 2-(benzo[b]thienyl)-5-phenylpyridine.

Bis[2-(5-phenylthiophene-2-yl)pyridine-C², N¹) (acetylacetonato)iridium (III) (Ex. Comp. No. 524).

Tris[2-(5-phenylthiophene-2-yl)pyridine-C², N¹)iridium (III) (Ex. Comp. No. 529).

As described above, according to the present invention, the metal coordination compound of the formula (1) characterized by aromatic substituent. The electroluminescence device (luminescence device) of the present invention using, as a luminescent center material, the metal coordination compound of the formula (1) is an excellent device which not only allows high-efficiency luminescence but also retains a high luminance for a long period and shows little deterioration by current passage. Further, the display apparatus using the electroluminescence device of the present invention exhibits excellent display performances.

What is claimed is:

1. A metal coordination compound represented by one of following formulas (a) or (b):

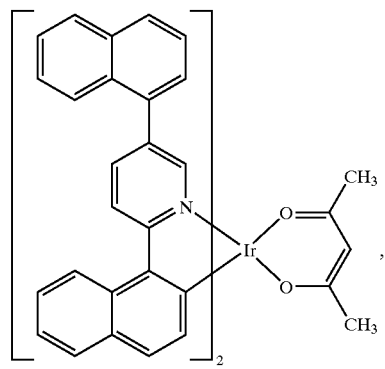

(a)

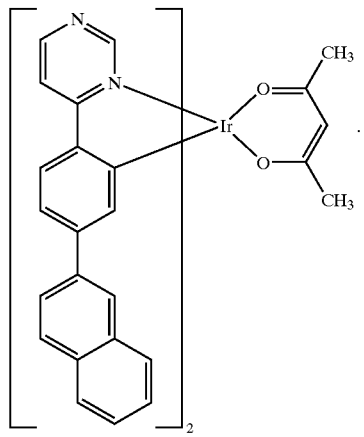

(b)

2. An electroluminescence device, comprising: a pair of electrodes disposed on a substrate, and a luminescence unit comprising at least one organic compound disposed between the electrodes, wherein the organic compound comprises a metal coordination compound represented by the formula (a) or (b) in claim 1.

3. The electroluminescence device according to claim 2, wherein a voltage is applied between the electrodes to emit light.

4. The electroluminescence device according to claim 2, wherein a voltage is applied between the electrodes to emit phosphorescence.

5. A picture display apparatus, comprising an electroluminescence device according to claim 2, and a means for supplying electric signals to the electroluminescence device.

6. A metal coordination compound represented by the following formula:

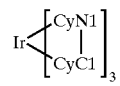

wherein CyN1 is a cyclic group having a nitrogen atom and is bonded to Ir via the nitrogen atom, and CyC1 is a cyclic group having a carbon atom and is bonded to Ir via the carbon atom and bonded to CyN1 via a covalent bond, at least one of CyN1 and CyC1 having the following substituent

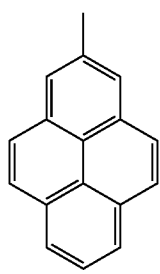

and either or both of CyN1 and CyC1 have an optional substituent selected from halogen, cyano, nitro, trialkylsilyl of which alkyl is independently a linear or branched alkyl group having 1 to 8 carbons or a linear or branched alkyl group having 1 to 20 carbons of which the alkyl group optionally includes one or non-neighboring two or more methylene groups that can be replaced with —O—, —S—, —CO—, —CO—O—, —O—CO—, —CH=CH— or C=C— and the alkyl group optionally includes a hydrogen atom that can be optionally replaced with a fluorine atom.

7. An electroluminescence device, comprising: a pair of electrodes disposed on a substrate, and a luminescence unit comprising at least one organic compound disposed between the electrodes, wherein the organic compound comprises a metal coordination compound represented by the formula in claim 6.

8. The electroluminescence device according to claim 7, wherein a voltage is applied between the electrodes to emit light.

9. The electroluminescence device according to claim 7, wherein a voltage is applied between the electrodes to emit phosphorescence.

10. A picture display apparatus, comprising an electroluminescence device according to claim 7, and a means for supplying electric signals to the electroluminescence device.

* * * * *